US010301596B2

(12) United States Patent
Hwang et al.

(10) Patent No.: US 10,301,596 B2
(45) Date of Patent: May 28, 2019

(54) METHOD OF REPAIRING DAMAGED CHONDROCYTES VIA LOW-DOSE IRRADIATION

(71) Applicant: KOREA INSTITUTE OF RADIOLOGICAL & MEDICAL SCIENCES, Seoul (KR)

(72) Inventors: Sang Gu Hwang, Seoul (KR); Eun Hee Hong, Seoul (KR)

(73) Assignee: KOREA INSTITUTE OF RADIOLOGICAL & MEDICAL SCIENCES, Seoul (KR)

(*) Notice: Subject to any disclaimer, the term of this patent is extended or adjusted under 35 U.S.C. 154(b) by 420 days.

(21) Appl. No.: 15/106,249

(22) PCT Filed: Dec. 24, 2014

(86) PCT No.: PCT/KR2014/012804
§ 371 (c)(1),
(2) Date: Jun. 17, 2016

(87) PCT Pub. No.: WO2015/099446
PCT Pub. Date: Jul. 2, 2015

(65) Prior Publication Data
US 2016/0362660 A1 Dec. 15, 2016

(30) Foreign Application Priority Data
Dec. 26, 2013 (KR) .................. 10-2013-0164277

(51) Int. Cl.
*A61N 5/10* (2006.01)
*C12N 5/077* (2010.01)

(52) U.S. Cl.
CPC ............ *C12N 5/0655* (2013.01); *A61N 5/10* (2013.01); *C12N 2501/2301* (2013.01);
(Continued)

(58) Field of Classification Search
CPC .................................. A61N 5/00; A61N 5/10
(Continued)

(56) References Cited

U.S. PATENT DOCUMENTS

| 2007/0014719 | A1* | 1/2007 | Reading | A61K 31/56 424/1.11 |
| 2011/0117202 | A1* | 5/2011 | Bourke, Jr. | H05B 41/2806 424/490 |
| 2014/0072538 | A1* | 3/2014 | Francki | A61K 35/50 424/93.7 |

FOREIGN PATENT DOCUMENTS

| JP | 2003518392 A | 6/2003 |
| JP | 2006167283 A | 6/2006 |

(Continued)

OTHER PUBLICATIONS

Kang, Ki-Hyun, et al., "Effects of irradiation on the calcific nodule formation in MC3T3-E1 osteoblastic cell line", Korean Journal of Oral and Maxillofacial Radiology, vol. 35, Mar. 31, 2005, pp. 1-8.
(Continued)

*Primary Examiner* — Samuel G Gilbert
(74) *Attorney, Agent, or Firm* — Greer, Burns & Crain, Ltd.; Gregory P. Einhorn

(57) ABSTRACT

The present invention relates to a method for inhibiting an inflammatory response in chondrocytes, and dedifferentiation or destruction of chondrocytes by irradiating damaged chondrocytes with low-dose radiation, and a method of treating a disease of cartilage by irradiating damaged chondrocytes with low-dose radiation.

17 Claims, 23 Drawing Sheets

(52) U.S. Cl.
CPC .. *C12N 2501/998* (2013.01); *C12N 2501/999* (2013.01); *C12N 2506/13* (2013.01); *C12N 2529/00* (2013.01)

(58) Field of Classification Search
USPC .......................................................... 600/1–8
See application file for complete search history.

(56) References Cited

FOREIGN PATENT DOCUMENTS

| | | |
|---|---|---|
| KR | 1020100051294 | 5/2010 |
| KR | 1020100061605 | 6/2010 |
| KR | 1020110134137 | 12/2011 |
| KR | 1020120051478 | 5/2012 |
| KR | 1020120111380 | 10/2012 |
| KR | 1020130047793 | 5/2013 |

OTHER PUBLICATIONS

Kim, Kyung-A., et al., "Effects of low dose irradiation on the calcific nodule formation in MC3T3-E1 osteoblastic cell line", vol. 34, Sep. 30, 2004, pp. 137-144.

Kihwan Moon, International Preliminary Report on Patentability dated Jun. 28, 2016.

World Intellecutal Property Organization, Written Opinion dated Apr. 7, 2015.

World Intellecutal Property Organization, International Search Report dated Apr. 7, 2015.

* cited by examiner

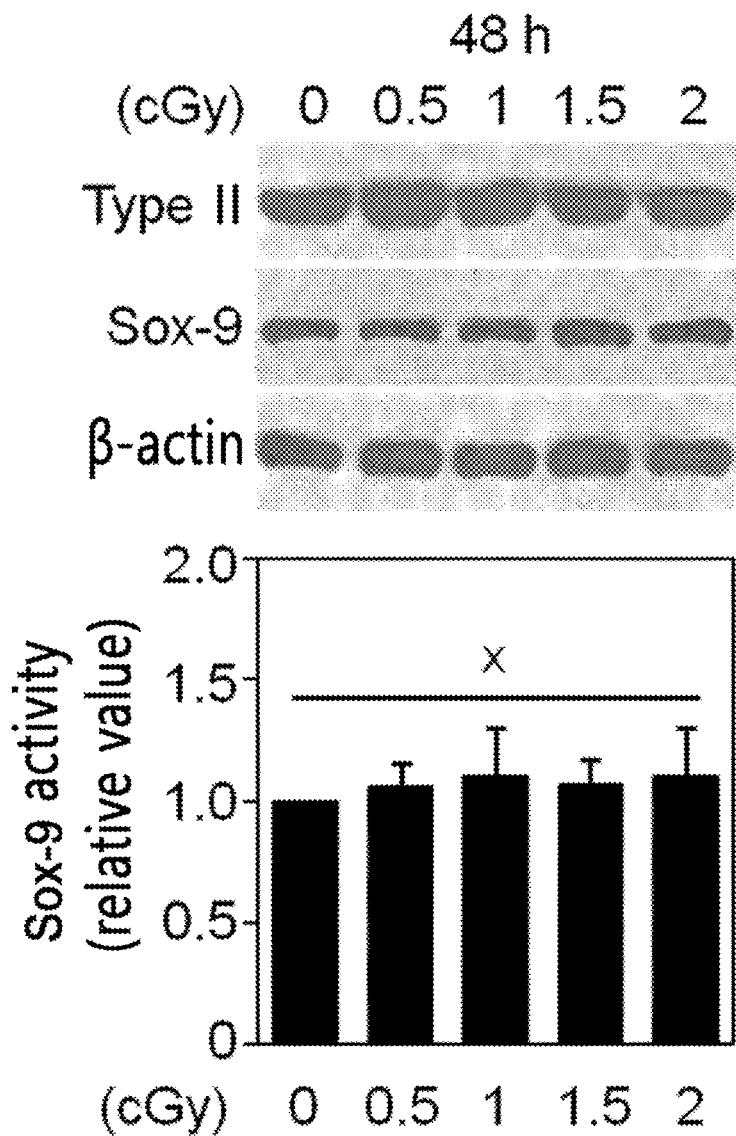
[FIG. 1a]

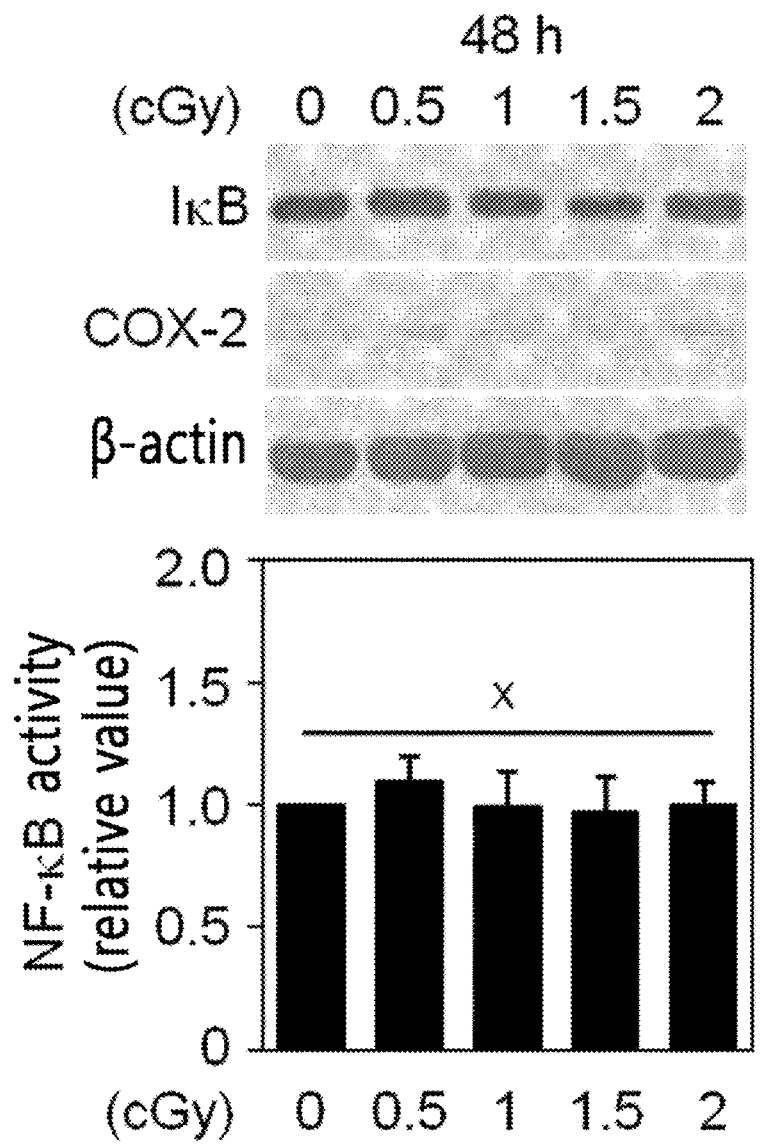
[FIG. 1b]

[FIG. 1c]
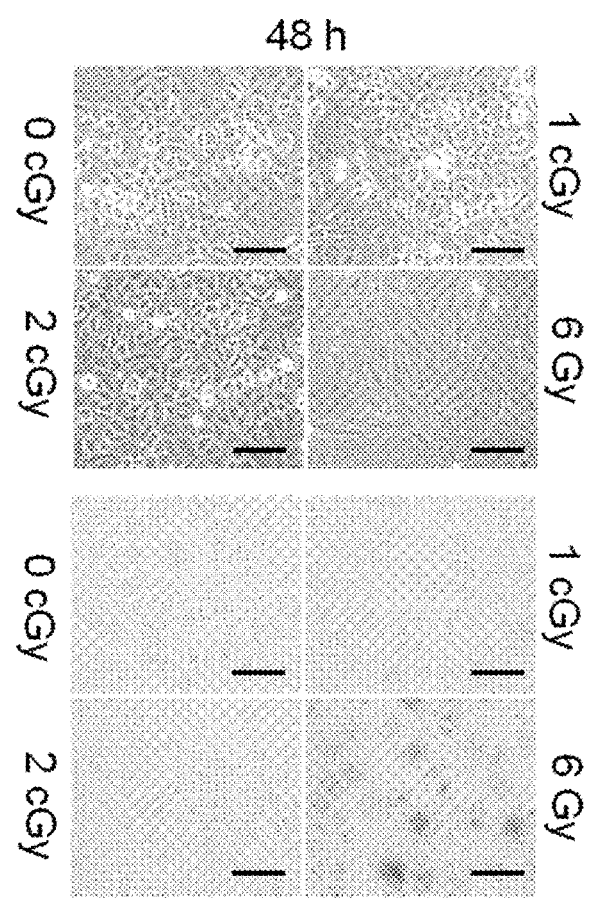

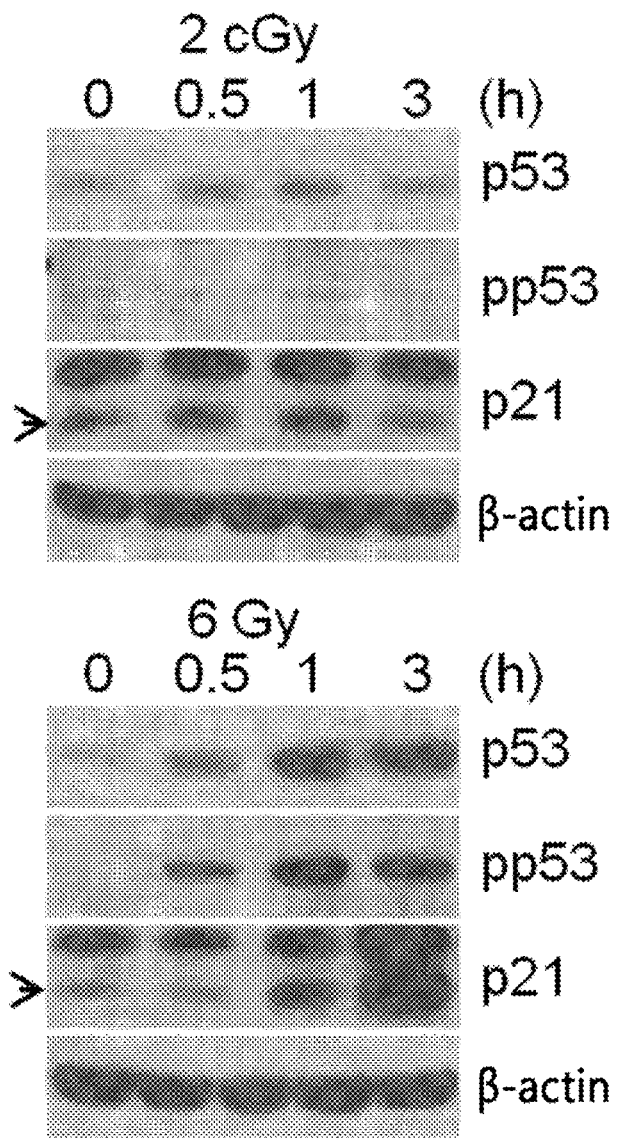

[FIG. 1e]
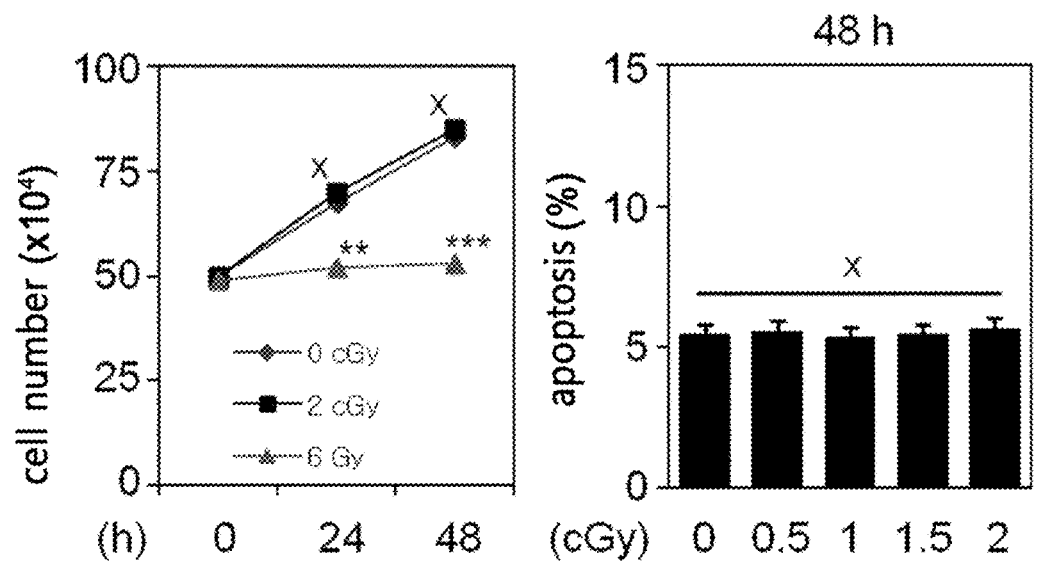
[FIG. 1f]
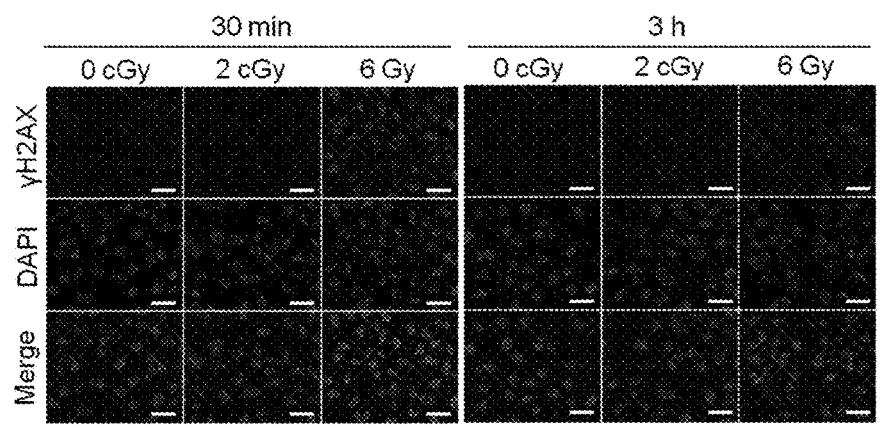

[FIG. 2a]
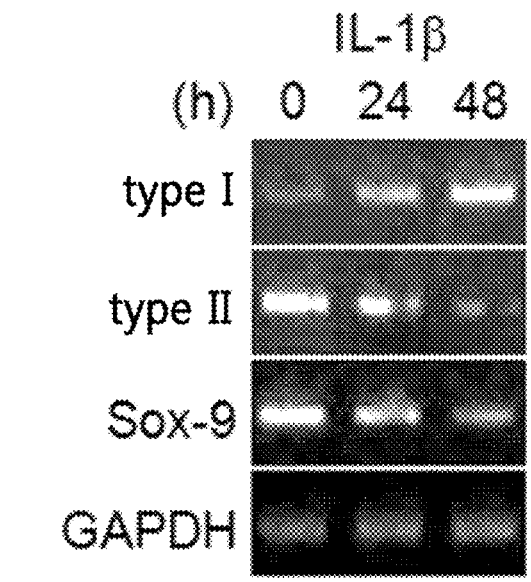
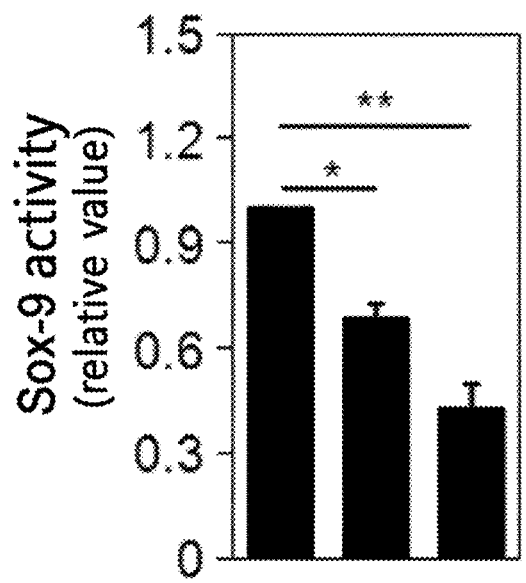
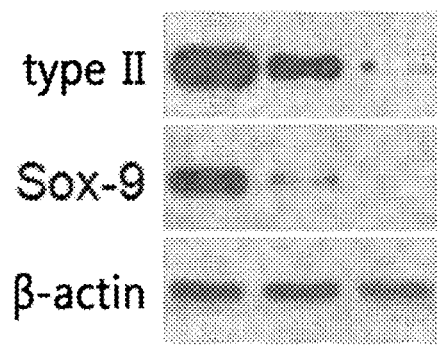

[FIG. 2b]
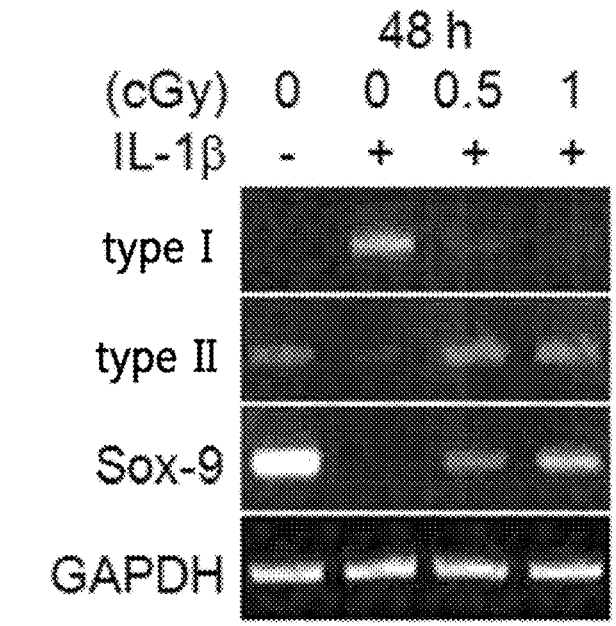
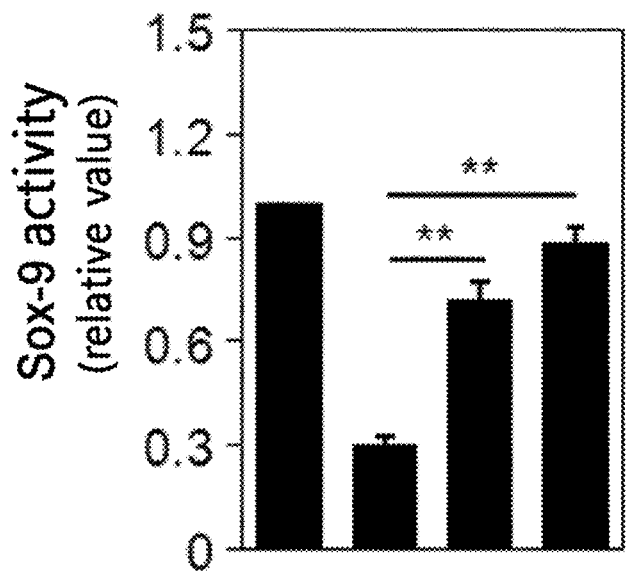
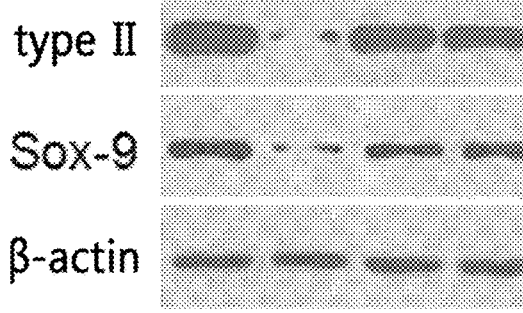

[FIG. 2c]
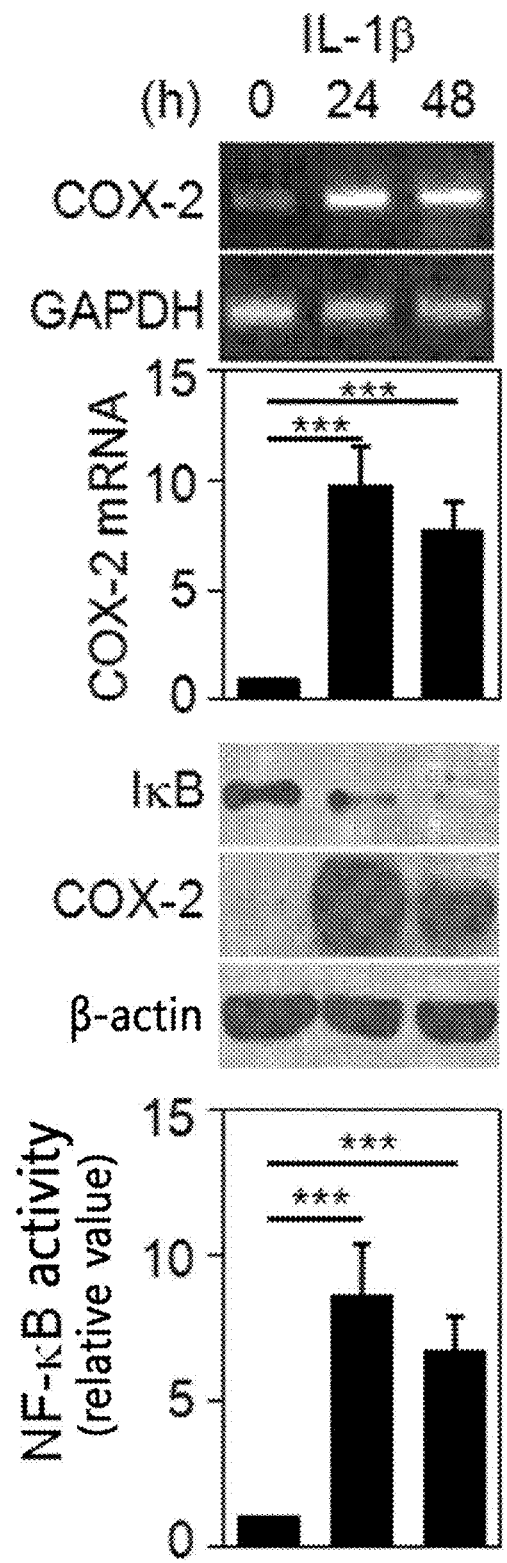

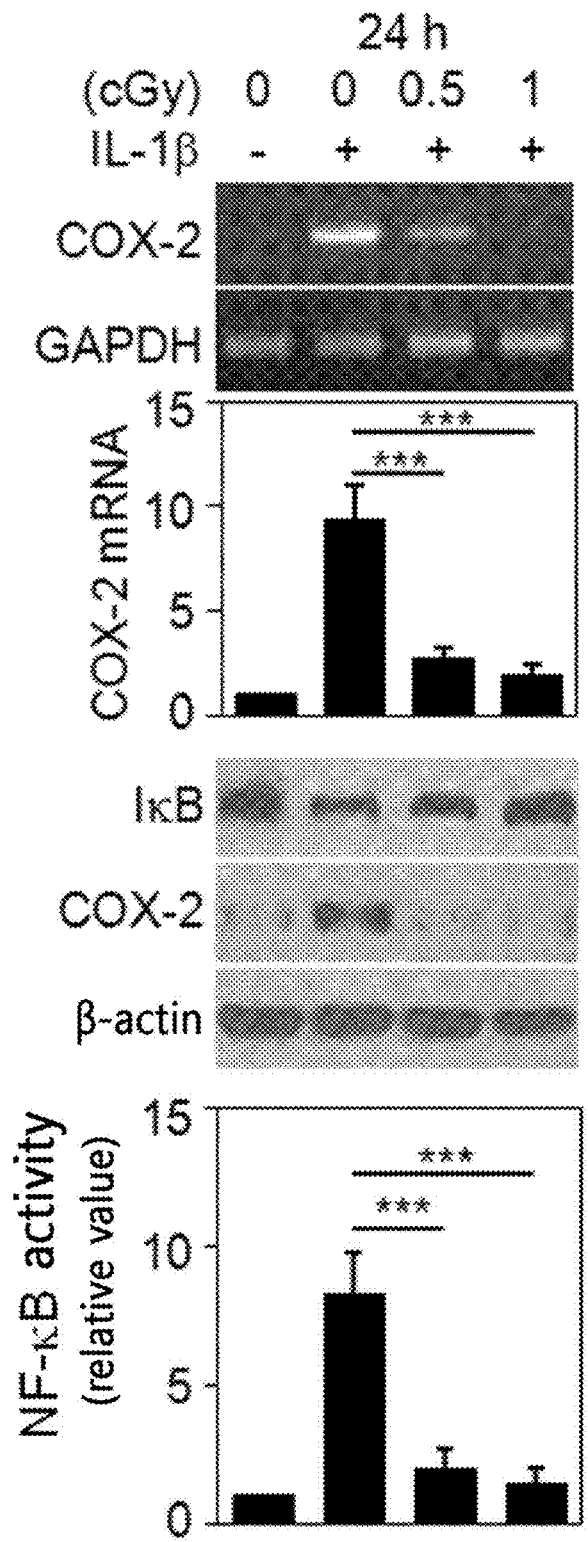
[FIG. 2d]

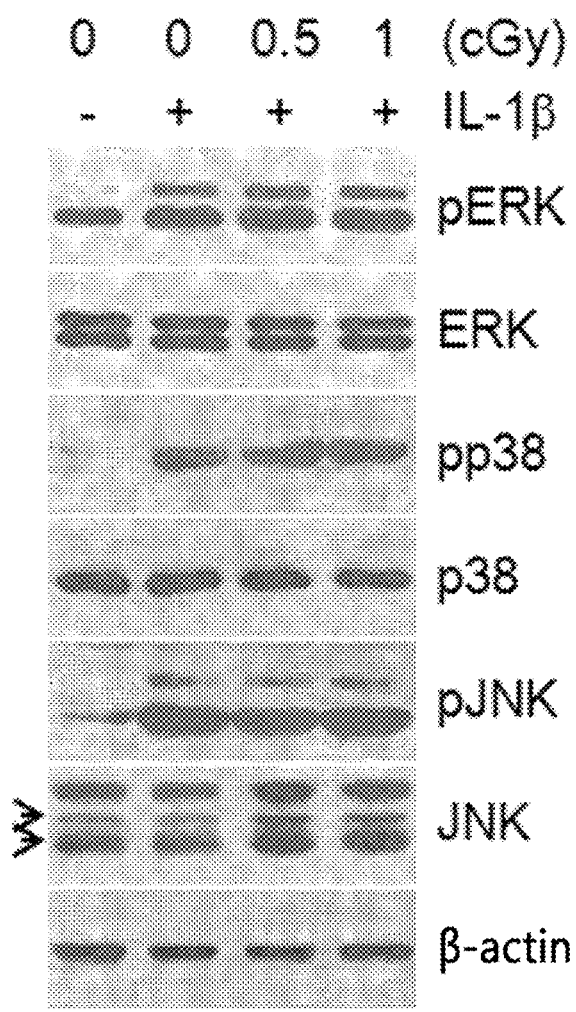
[FIG. 3a]

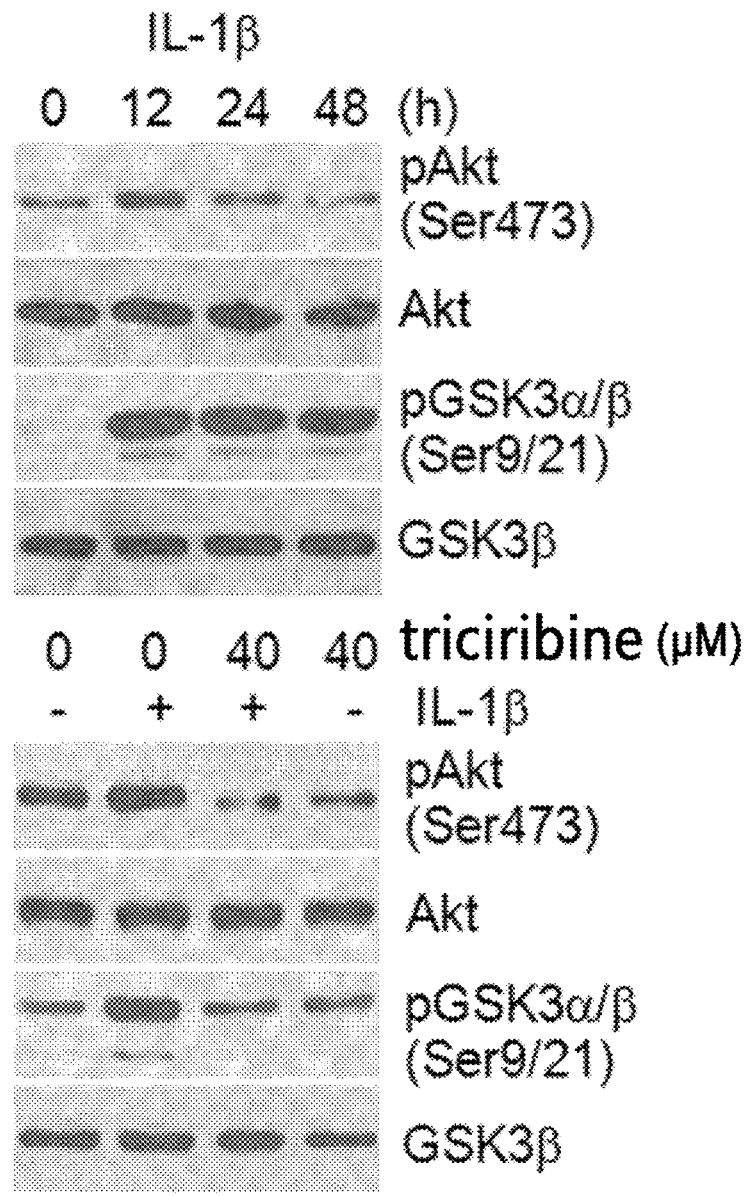

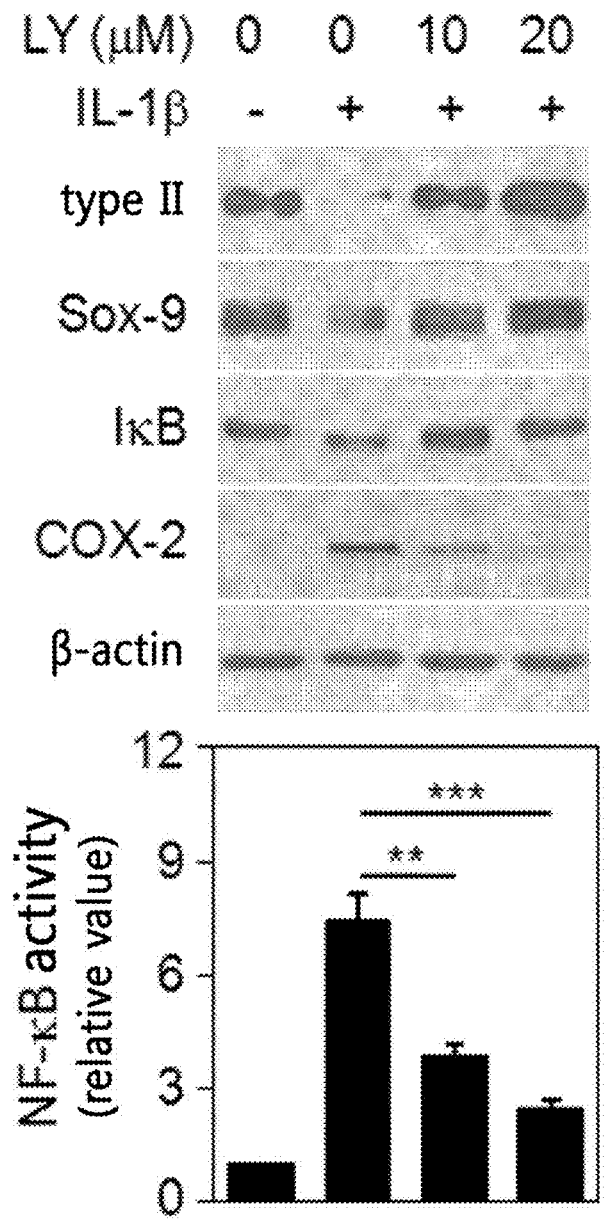
[FIG. 3c]

[FIG. 3d]
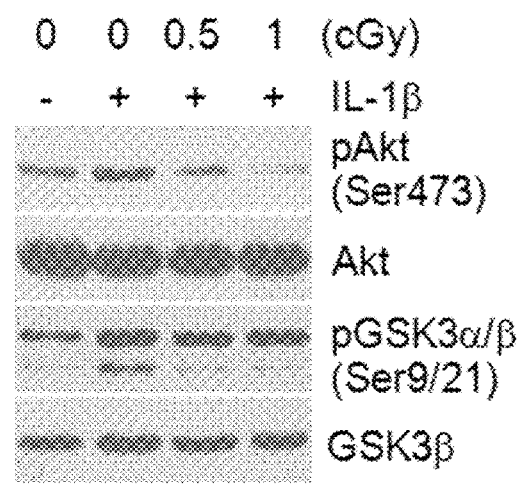

[FIG. 4a]
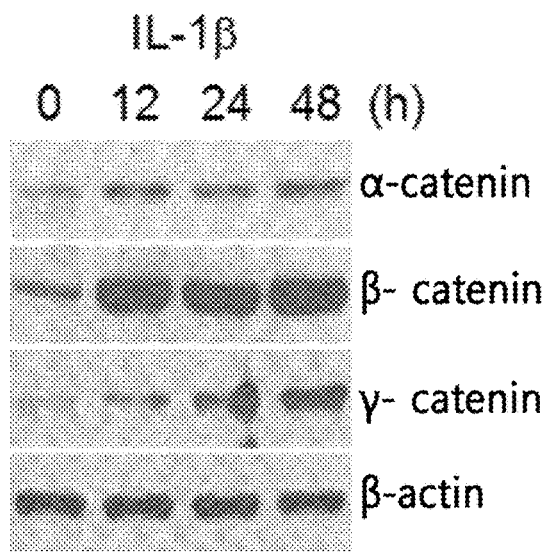
[FIG. 4b]
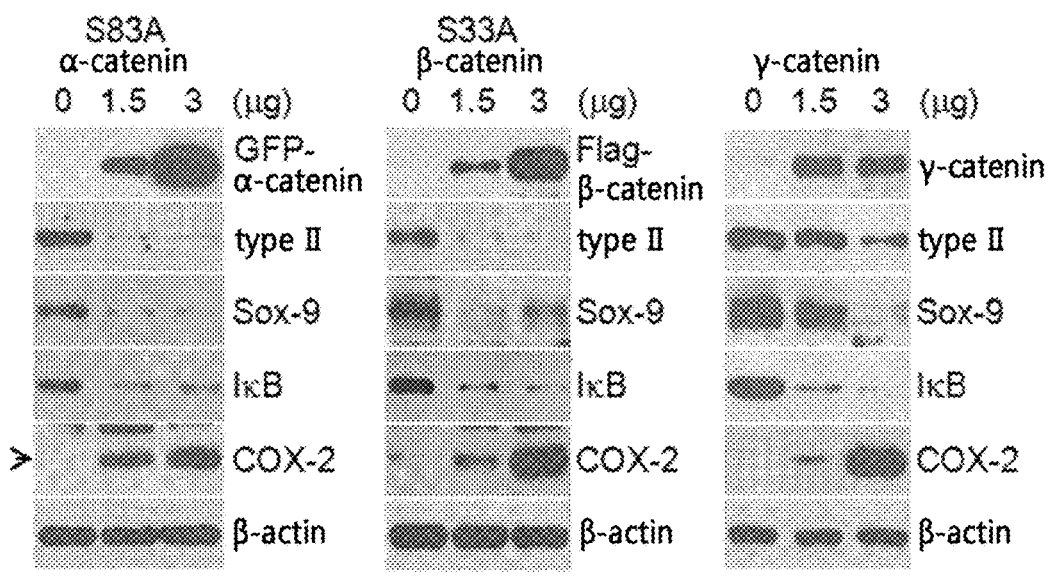

[FIG. 4c]
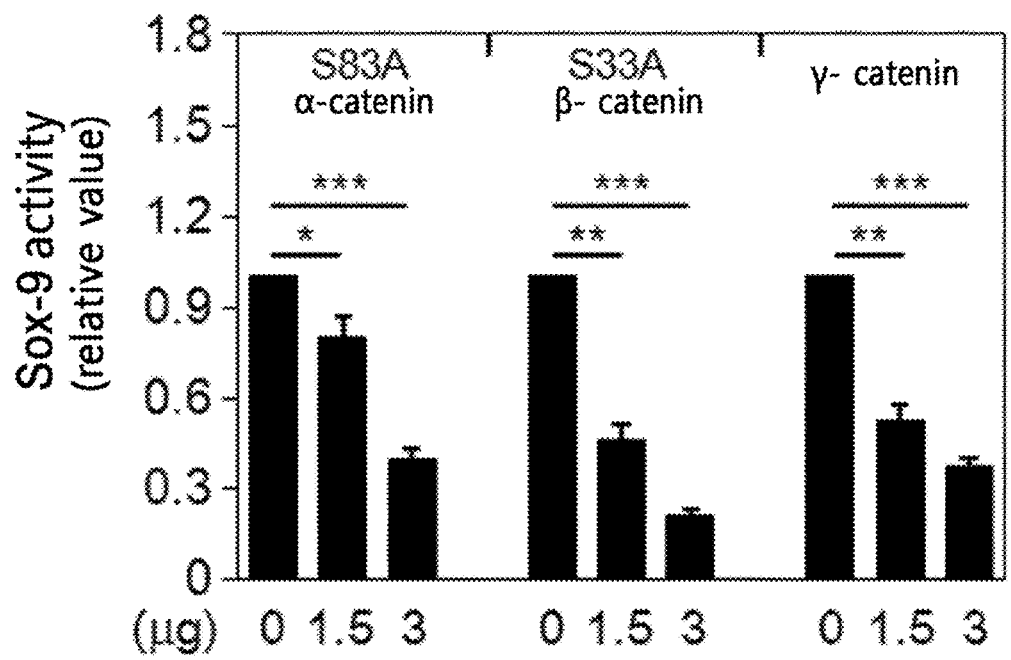
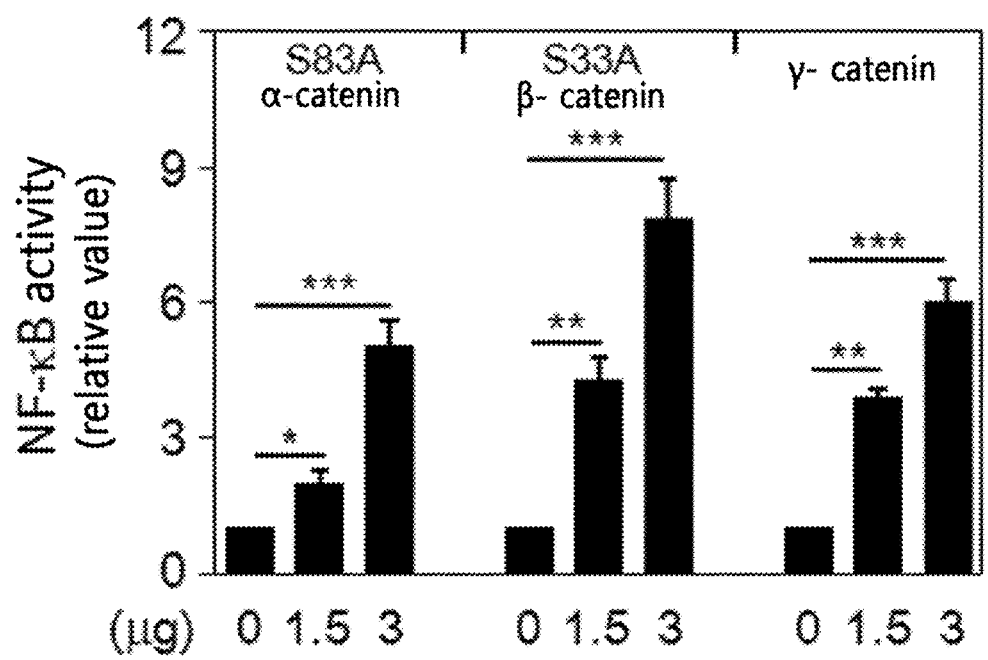

[FIG. 4d]
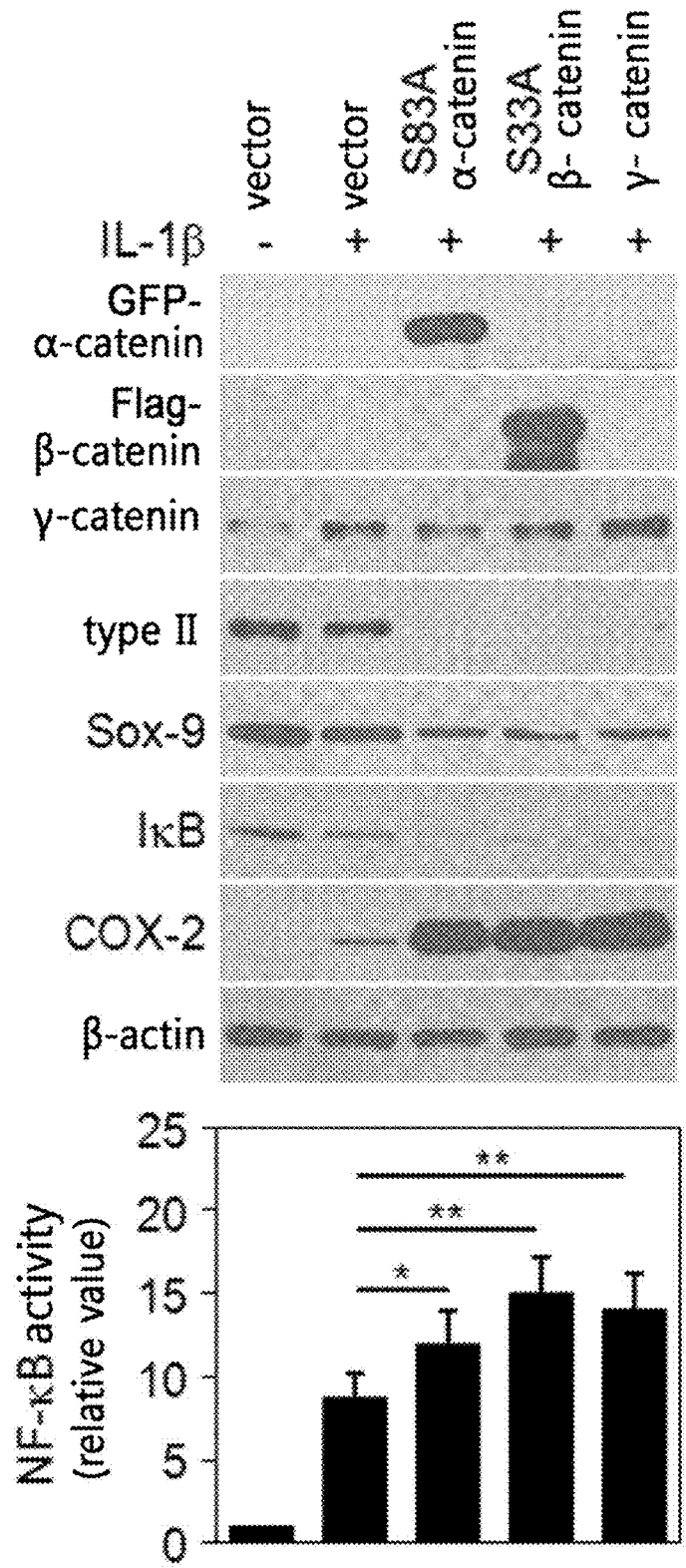

[FIG. 5a]
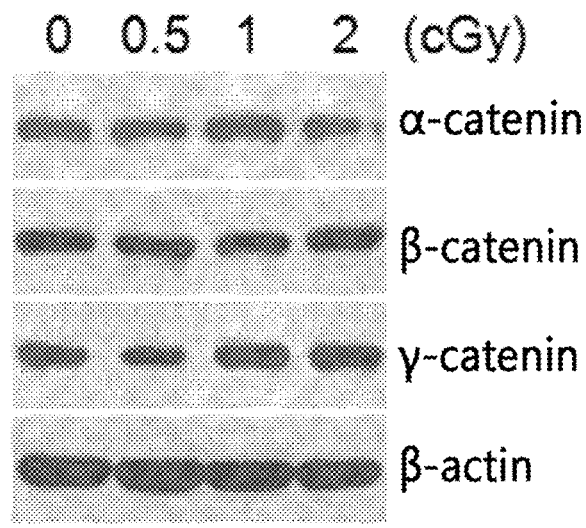
[FIG. 5b]
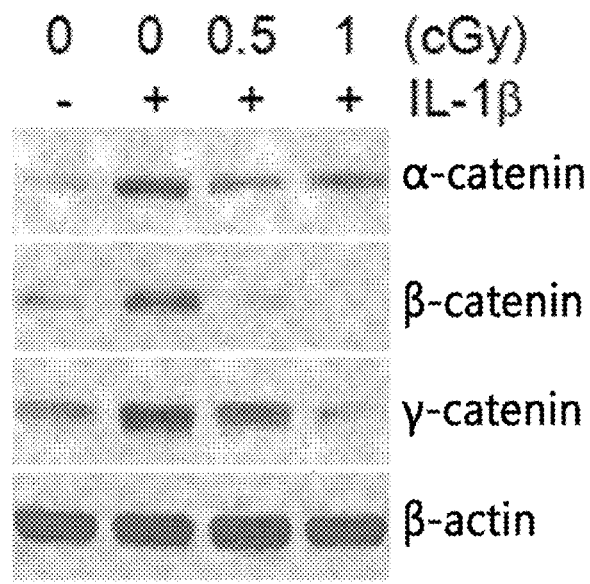

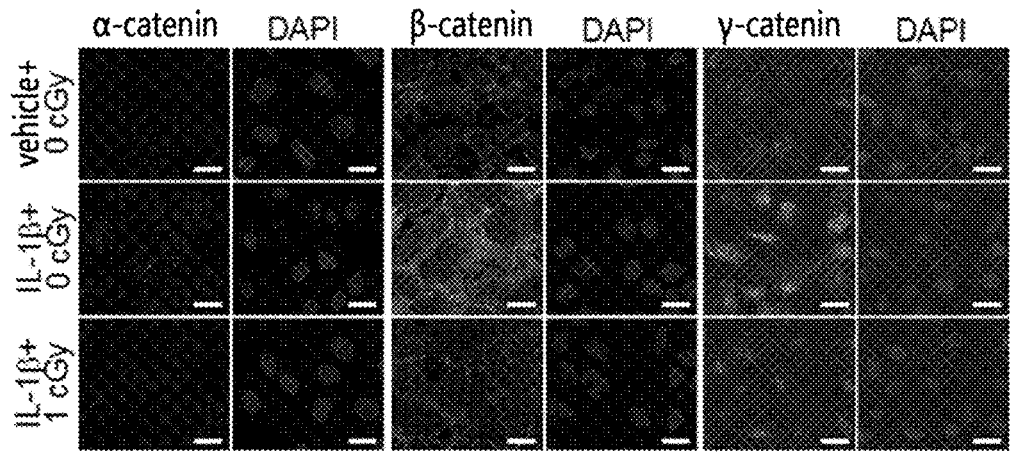
[FIG. 5c]
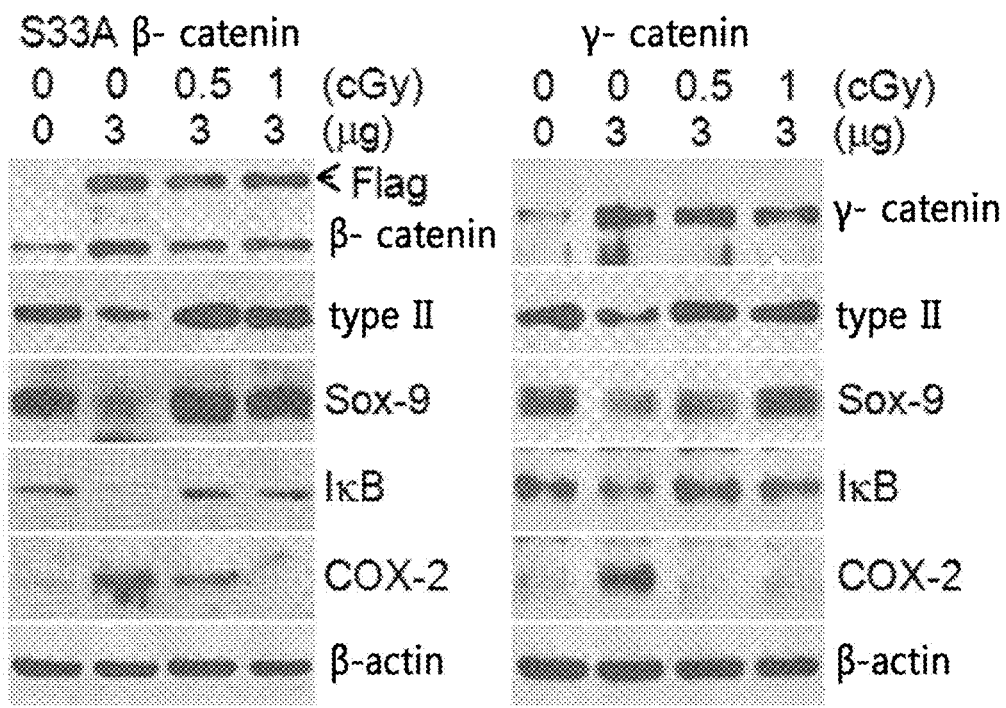
[FIG. 5d]

[FIG. 5e]
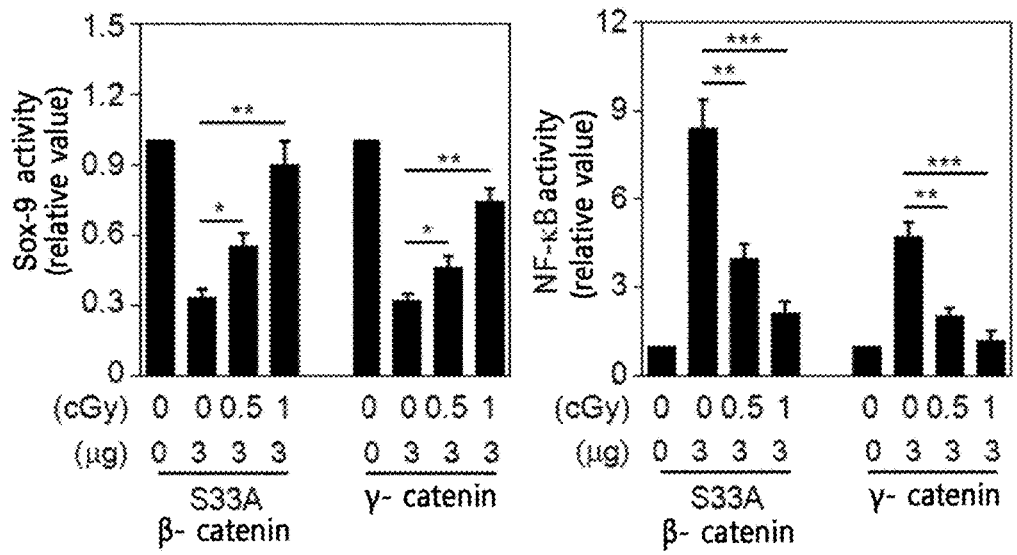
[FIG. 5f]
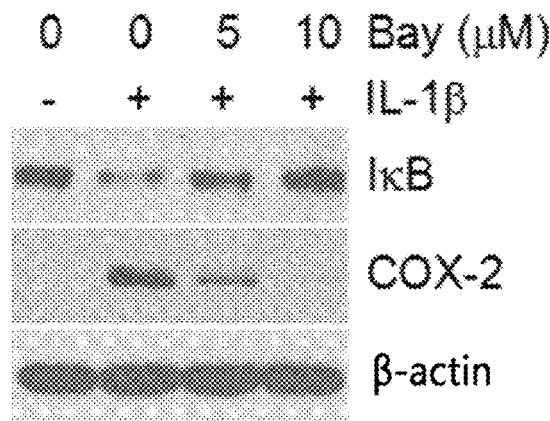

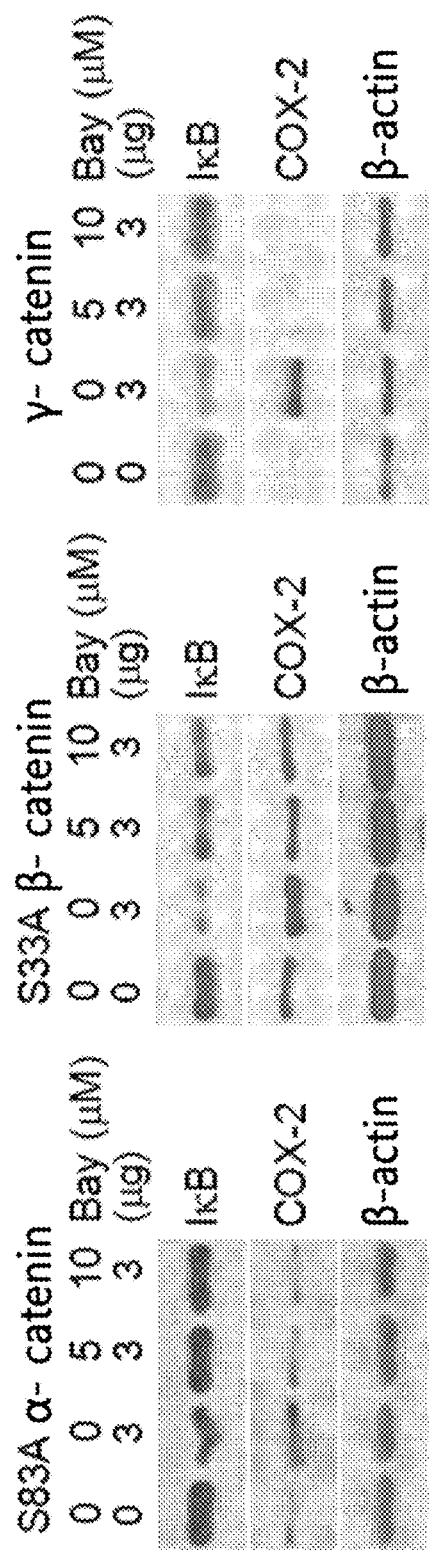
[FIG. 5g]

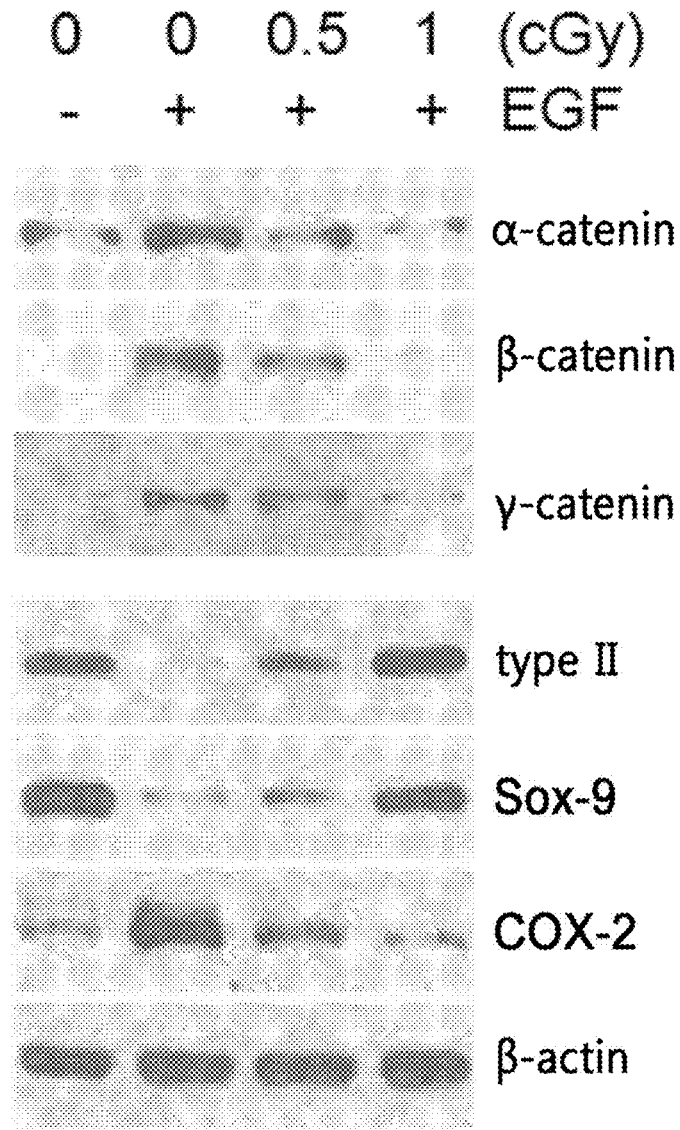

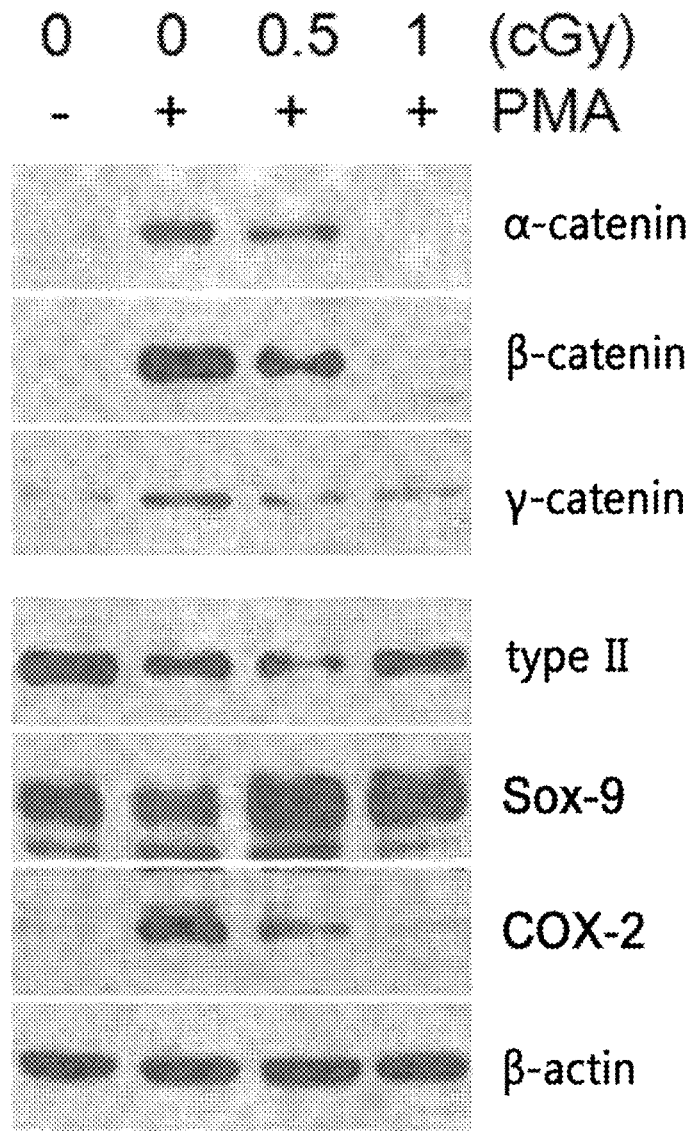

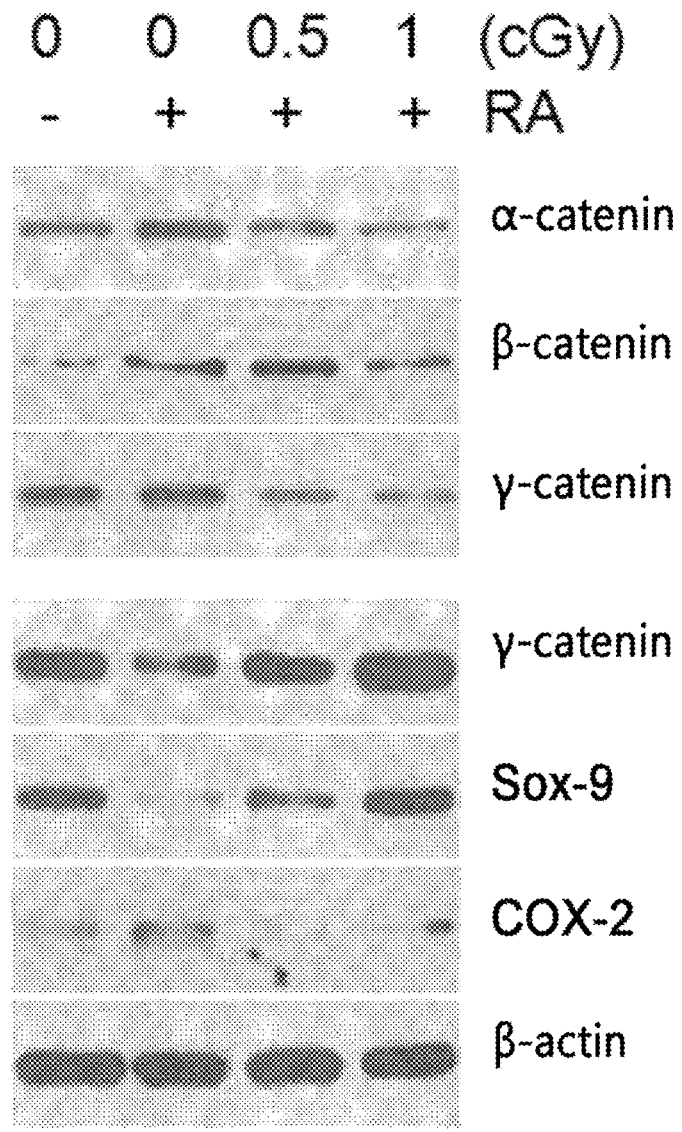

METHOD OF REPAIRING DAMAGED CHONDROCYTES VIA LOW-DOSE IRRADIATION

This application is a national phase application claiming benefit of priority under 35 U.S.C. § 371 to International (PCT) Patent Application serial number PCT/KR2014/012804, filed Dec. 24, 2014, which claims benefit of priority to Korean Application 10-2013-0164277, filed Dec. 26, 2013. The aforementioned applications are expressly incorporated herein by reference in their entirety and for all purposes.

BACKGROUND OF THE INVENTION

1. Field of the Invention

The present invention relates to a method for inhibiting an inflammatory response in chondrocytes, and dedifferentiation or destruction of chondrocytes by irradiating damaged chondrocytes with low-dose radiation, and a method of treating a disease of cartilage by irradiating damaged chondrocytes with low-dose radiation.

2. Description of the Related Art

From the embryological point of view, cartilage is a tissue originated from a mesoderm such as a hard bone tissue, and forms an endoskeleton along with bones. Additionally, in the case of serious cartilage damage, the bone tissues below the cartilage may also be damaged. In particular, in the case of an articular cartilage, which has no blood vessels, neurons, and lymphoid tissues, once there is damage to the cartilage, self-regeneration of the articular cartilage is difficult. Accordingly, even the slightest damage to articular cartilage may progress further and degenerate. In this regard, various medical attempts are being made in order to recover and maintain the functions of bones and cartilage tissues.

Arthritis, a representative disease caused by cartilage damage, is a kind of degenerative disease. Reportedly, arthritis occurs in about 80% of people in Korea aged 55 or older, and in almost all people aged 70 or older, and expedited development of its therapeutic treatments is currently underway. Currently available clinical methods for treating damaged areas of articular cartilage include multiple drilling, microfracture, abrasion, transplantation of periosteum or perichondrium, etc. However, their therapeutic effects are not satisfactory, and thus active studies on new methods of treatment are in progress.

Recently, a method of inducing stem cells into chondrocytes, a method of transplanting an autologous or allogeneic cartilage tissue into a cartilage damaged area, a method of transplanting a tissue or compound, which is capable of inducing cartilage, onto the surface of the cartilage damaged area, a method of regenerating cartilage by transplanting chondrocytes into the cartilage damaged area, etc., are developed, and their preclinical or clinical test results are also reported. For example, Korean Patent Application Publication No. 2010-0051294 discloses a cell aggregate-hydrogel-polymer scaffold complex useful for cartilage regeneration, in which cell aggregates of differentiated chondrocytes are dispersed in a hydrogel matrix, and the resulting hydrogel matrix is inoculated onto a polymer scaffold and the pores thereof are filled with the cell aggregate-hydrogel-polymer scaffold complex, a method for its preparation, and a composition for treating the cartilage defects and injuries comprising the same as an active ingredient. Korean Patent Application Publication No. 2010-0061605 discloses a chondrogenic differentiation method from a mesenchymal stein cell and a composition comprising chondrogenic cell for repairing disease of cartilage damage. However, these methods have various problems in that they require an excess of time for the transplanted tissues to adapt or regenerate in a new living organism, there may occur an immune rejection response in the case of a transplanted tissue, and also that the transplanted or regenerated tissue may not be accurately settled to the original cartilage site, thus causing an aftereffect such as a lumbar herniated intervertebral disc, and are thus not yet being used in practical treatments.

SUMMARY OF THE INVENTION

Under these circumstances, the present inventors have endeavored to develop a method for treating diseases caused by the inflammation of damaged cartilage without adverse effects, and have discovered that irradiation of damaged cartilage with low-dose radiation (LDR) can recover the damaged cartilage without adverse effects, thus completing the present invention.

An object of the present invention is to provide a method for inhibiting the inflammatory response in chondrocytes via irradiation with low-dose radiation (LDR).

Another object of the present invention is to provide a method for inhibiting the dedifferentiation of chondrocytes via irradiation with low-dose radiation (LDR).

Still another object of the present invention is to provide a method for inhibiting the destruction of chondrocytes via irradiation with low-dose radiation (LDR).

Still another object of the present invention is to provide a method for treating a disease of cartilage via irradiation with low-dose radiation (LDR).

Advantageous Effects

The method of the present invention employing low-dose radiation (LDR) enables repair of damaged cartilage, and can thus be used for the treatment of inflammatory diseases of cartilage.

BRIEF DESCRIPTION OF THE DRAWINGS

FIGS. 1a through 1f illustrate the effect of low-dose radiation (LDR) on the phenotypes of chondrocytes. Chondrocytes were irradiated with a varied amount of radiation under each experimental condition. The levels of differentiation-related proteins (FIG. 1a, top) and inflammation-related proteins (FIG. 1b, top) were determined via Western blot analysis. The transcriptional activity of Sox-9 (FIG. 1a, bottom) and the transcriptional activity of NE-κB (FIG. 1b, bottom) were determined via gene analysis. The experimental results were indicated in terms of mean±standard deviation, and x represents no significance relative to the untreated control group. The change in cell shape was observed under optical microscope (FIG. 1c, top; scale: 1 mm), and cell senescence was evaluated by senescence-associated β-galactosidase (SA-β-gal) positive staining (blue, FIG. 1c, bottom; scale: 1 mm). The level of senescence-related proteins was determined via Western blot analysis (FIG. 1d). The total cell number was quantitated by counting the number of viable cells using a trypari blue solution (FIG. 1e, left), and cell apoptosis was determined via FACS analysis (FIG. 1e, right). The experimental results were indicated in terms of mean±standard deviation ($p<0.005$, *$p<0.0005$), and x represents no significance relative to the untreated control group. The phosphorylation of H2AX was determined by confocal fluorescence microscope, and cell nuclei were confirmed by staining with 4',6-diamidino-2-phenylindole (FIG. 1f, scale: 40 μm).

FIGS. 2a through 2d illustrate the inhibitory effect of LDR against the IL-1β-induced destruction of chondrocytes. The chondrocytes were treated with 10 ng/mL of IL-1β alone (FIGS. 2a and 2c) or with a combination of 0.5 cGy or 1 cGy LDR for a predetermined period of time (FIGS. 2b and 2d). The transcription level of dedifferentiation-related genes was determined by PCR using GAPDH as a control (FIGS. 2a and 2b, top). The transcriptional activity of Sox-9 was determined by reporter gene assay. The experimental results were indicated in terms of mean±standard deviation (FIG. 2a (middle) shows *p<0.05 and p<0.005 relative to the untreated control group; and FIG. 2b (middle) shows p<0.005 relative to cells treated with IL-1β alone). The levels of type II collagen and Sox-9 proteins were detected via Western blot analysis (FIGS. 2a and 2b, bottom). The level of COX-2 transcript was determined via normal PCT, which used GAPDH as a control, and a quantitative real-time PCT. The experimental results were indicated in terms of mean±standard deviation (FIG. 2c (top) shows *p<0.0005 relative to a control group; and FIG. 2d (top) shows *p<0.0005 relative to cells treated with IL-1β alone). The levels of I-κB and COX-2 proteins were detected via Western blot analysis (FIGS. 2c and 2d (middle)). The transcriptional activity of NF-κB was determined by reporter gene assay. The experimental results were indicated in terms of mean±standard deviation (FIG. 2c (bottom) shows *p<0.0005 relative to the untreated control group; and FIG. 2d (bottom) shows *p<0.0005 relative cells treated with IL-1β alone).

FIGS. 3a through 3d illustrate the correlation of PI3K/Akt signaling regarding the inhibition of LDR-mediated chondrocyte destruction. (FIG. 3a) Chondrocytes, in a state untreated (−) or treated with 10 ng/mL, IL-1β (+), were treated with 0.5 cGy or 1 cGy LDR. The levels of expression and phosphorylation of ERK, p38, and INK were determined via Western blot analysis. (FIG. 3b) Chondrocytes were treated with 10 ng/mL IL-1β for a predetermined period of time (top), and 1 hour before IL-1β treatment, were treated with 40 tricibidine or untreated (bottom). The levels of expression and phosphorylation of Akt and GSK3α/β were determined via Western blot analysis. (FIG. 3c) Chondrocytes, 1 hour before treatment with 10 ng/mL IL-1β, were untreated or treated with 10 μM or 20 μM LY294002. After 48 hours, the levels of type II collagen, Sox-9, I-κB and COX-2 proteins were determined via Western blot analysis (top). The transcriptional activity of NF-κB was determined by reporter gene assay. The experimental results were indicated in terms of mean±standard deviation (the bottom shows p<0.005 and *p<0.0005 relative to cells treated with IL-1β alone). (FIG. 3d) Chondrocytes, in a state untreated (−) or treated with 10 ng/mL (+), were treated with 0.5 cGy or 1 cGy LDR for 12 hours. The levels of expression and phosphorylation of Akt and GSK3α/β were determined via Western blot analysis.

FIGS. 4a through 4d illustrate the roles of IL-1β-induced catenin proteins on chondrocyte destruction. (FIG. 4a) Chondrocytes were treated with 10 ng/mL IL-1β for a predetermined period of time. The level of catenin protein was determined via Western blot analysis, (FIGS. 4b and 4c) Chondrocytes, in a state treated with Sox-9 or untreated (FIG. 4c, left), or treated with an NF-κB reporter gene or untreated (FIG. 4c, right), were introduced with GFP-labeled S83A α-catenin, FLAG-labeled S33A β-catenin, or wild type γ-catenin. The levels of differentiation- and inflammation-related proteins were determined via Western blot analysis (FIG. 4b), and the transcriptional activity of Sox-9 or NF-κB was determined by reporter gene assay. The experimental results were indicated in terms of mean standard deviation (FIG. 4c shows *p<0.05, p<0.005 and *p<0.0005 relative to the untreated control group). (FIG. 4d) Chondrocytes were introduced with 3 μg of catenin plasmid for 24 hours, respectively, and treated with 10 ng/mL IL-1β (+) or untreated (−) for 48 hours. The levels of differentiation- and inflammation-related proteins were determined via Western blot analysis (top), and the transcriptional activity of NF-κB was determined by reporter gene assay at 24 hours after IL-1β treatment. The experimental results were indicated in terms of mean standard deviation (bottom, *p<0.05 and **p<0.005 relative to cells treated with IL-1β alone).

FIGS. 5a through 5g illustrate the effects of LDR on the IL-1β-induced catenin expression and the catenin-induced cartilage destruction. (FIGS. 5a and 5b) Chondrocytes, in a state untreated with 10 ng/mL IL-1β (FIG. 5a) or treated with 10 ng/mL IL-1β (FIG. 5b), were irradiated with LDR at varied doses of radiation for 48 hours. The level of catenin protein was determined via Western blot analysis. (FIG. 5c) Chondrocytes, in a state treated with 10 ng/mL IL-1β or untreated, were treated with 1 cGy LDR for 48 hours or untreated. The expression level of each catenin was detected via confocal fluorescence microscope (scale: 50 μm). (FIGS. 5d and 5c) Chondrocytes were introduced with 3 μg of FLAG-labeled S33A β-catenin or wild type γ-catenin, and then irradiated with LDR at varied doses of radiation for 48 hours. The levels of differentiation- and inflammation-related proteins were determined via Western blot analysis (FIG. 5d). The transcriptional activity of Sox-9 (FIG. 5e, left) or NT-κB (FIG. 5e, right) was determined by reporter gene assay. The experimental results were indicated in terms of mean±standard deviation (FIG. 5e, *<0.05, p<0.005 and *p<0.0005 relative to cells treated with IL-1β alone). (FIG. 5f) Cells, 1 hour before 10 ng/mL, IL-1β treatment, were treated with 5 μM or 10 μM Bay 11-7082 or untreated. After 48 hours, the levels of I-κB and COX-2 proteins were determined via Western blot analysis. (FIG. 5g) Chondrocytes were introduced with 3 μg of GFP-labeled S83A α-catenin (left), FLAG-labeled S33A β-catenin (middle), or a wild type γ-catenin (right), and then treated with 5 μM or 10 μM Bay 11-7082 for 24 hours or untreated. The levels of I-κB and COX-2 proteins were determined via Western blot analysis.

FIGS. 6a through 6c illustrate the inhibitory effect of LDR against the soluble factor-induced chondrocyte destruction. Chondrocytes were untreated or treated with 10 ng/mL EGF (FIG. 6a), 10 nM PMA (FIG. 6b), and 1 μM RA (FIG. 6c) for 2 hours, and then irradiated with 0.5 cGy or 1 cGy LDR for 36 hours or unirradiated. The levels of catenin proteins (top) and the levels of differentiation/inflammation-related proteins (bottom) were determined via Western blot analysis.

DETAILED DESCRIPTION OF THE PREFERRED EMBODIMENTS

In an aspect, the present invention provides a method for inhibiting inflammatory response in chondrocytes and dedifferentiation and destruction of chondrocytes, including a step of irradiating the chondrocytes with low-dose radiation (LDR).

The present inventors, while endeavoring various efforts to develop a method for treating diseases due to the inflammation of damaged cartilage, have noted the importance of low-dose radiation (LDR). As a result, unlike high-dose radiation (HDR), which can induce damage to chondrocytes, the irradiation of chondrocytes with LDR at a dose of 2 cGy or below was confirmed to be safe, not causing any damage to chondrocytes, and could also inhibit the dedifferentiation, inflammation, and destruction of chondrocytes induced by IL-1β treatment. Specifically, the inhibitions can be executed by blocking the IL-1β-induced PI3K/Akt signaling pathway instead of the MAPK pathway, and LDR irradiation was shown to inhibit the IL-1β-induced dedifferentiation, the inflammation-inducing catenin-induced dedifferentiation and inflammation of chondrocytes, and EGF-, PMA- and RA-induced dedifferentiation and inflammation. Accordingly, when LDR irradiation is used alone or in combination with a known therapeutic agent at the occurrence of a disease of cartilage accompanying damage of chondrocytes, LDR was shown to effectively treat the disease.

As such, the present invention provides a method for inhibiting the inflammatory response, dedifferentiation, or inflammation of chondrocytes, including a step of irradiating chondrocytes with low-dose radiation. According to an exemplary embodiment of the present invention, the chondrocytes may be those separated from a living organism, but are not limited thereto.

As used herein, the term "low-dose radiation (LDR)" refers to an amount of radiation, which, when chondrocytes are irradiated therewith, can inhibit the inflammatory response, dedifferentiation, and/or destruction of chondrocytes. Specifically, the low-dose radiation is not particularly limited as long as it can inhibit the inflammatory responses, dedifferentiation, and/or destruction of chondrocytes if the chondrocytes are irradiated therewith. Preferably, however, LDR is used at a minimum dose of radiation, and for its application to an individual, it may be in the range of greater than 0 Gy (gray) and 1 Gy or less, and specifically, in the range of greater than 0 Gy and 0.5 Gy or less. Additionally, when applied to separated cells, LDR may be in the range of greater than 0 cGy (centigray) and 2 cGy or less. The low-dose radiation may be used to induce a hormesis phenomenon, and in the present invention, long-term continuous irradiation of chondrocytes with LDR may not induce damage to chondrocytes. The duration of LDR irradiation may not be particularly limited, but preferably, for 6 hours to 90 hours, more preferably for 24 hours to 72 hours, and most preferably for 48 hours.

In the present invention, LDR irradiation can not only recover the decreased level of I-κB protein and the increased level of COX-2 protein, both caused by inflammatory responses, to their normal levels, but also recover the inhibited expression levels of type II collagen and Sox-9 proteins, accompanied by the dedifferentiation or destruction of chondrocytes, and the increased expression level of COX-2 protein and the transcriptional activity of NF-κB, back to their normal states. Accordingly, the irradiation of chondrocytes with LDR according to the method of the present invention can inhibit the inflammatory responses, dedifferentiation, or destruction of chondrocytes, and these inhibitory effects of LDR irradiation against the inflammatory responses, dedifferentiation, or destruction of chondrocytes were first disclosed in the present invention.

As used herein, the term "chondrocytes" refers to cells which, being present within chonrin, synthesize and secrete cartilage matrices. Structurally, rough endoplasmic reticulum and golgi apparatus, etc., are developed within the chondrocytes, and their external appearance is the same as that of lacunae. The chondrocytes may be present in an oblong or flat form, below a perichondrium or in the surface layer of joint cartilage, and in a semi-circle or polygon in the deep core part. Because the cell membranes of the chondrocytes are connected to polysaccharides or protein complexes, and these complexes are stereoscopically connected to the polysaccharides or fibers of the matrices, the chondrocytes exist in a floating state and thus can exhibit a significant level of buffering effect against external shocks.

According to an exemplary embodiment of the present invention, the inflammatory responses, dedifferentiation, and destruction of chondrocytes may be caused by cytokines, and specifically, may be induced by signaling mediated by IL-1β or catenin proteins.

IL-1β can increase the expression of type I collagen in chondrocytes, reduce the expressions of type II collagen and Sox-9, and activate the inflammatory signaling such as COX-2. Additionally, IL-1β can induce the expressions of α-, β-, and γ-catenin proteins, thereby causing inflammatory responses, dedifferentiation, and destruction of chondrocytes.

However, the causes of the inflammatory responses, dedifferentiation, and destruction of chondrocytes are not restricted thereto, but they may be induced by epidermal growth factor (EGF), phorbol 12-myristate 13-acetate (PMA), retinoic acid (RA), or a combination thereof, in addition to IL-1β. The above-described EGF, PMA, and RA can increase the expression of catenin proteins, thereby causing destruction, dedifferentiation, and inflammation of chondrocytes.

The above method can also be conducted under in vitro or ex vivo condition, in addition to an in vivo condition.

According to an exemplary embodiment of the present invention, first, as a result of the analysis of the effects of HDR and LDR on chondrocytes by respectively irradiating cultured chondrocytes with HDR and LDR, it was confirmed that, unlike HDR irradiation, LDR irradiation did not induce any change in the transcriptional activities of differentiation markers and inflammation-related markers (FIGS. 1a and 1b), did not change the shape of chondrocytes or induce cell senescence (FIG. 1c), did not increase the expression level of senescence-related proteins (FIG. 1d), neither inhibited the proliferation of chondrocytes nor increased the apoptotic rate of chondrocytes (FIG. 1e), and did not damage the DNA of chondrocytes (FIG. 1f).

Then, as a result of the analysis of the inhibitory effects of LDR on induced chondrocyte destruction, it was confirmed that the phenomena of promoting the dedifferentiation of chondrocytes such as the induction of expression of fibrous type I collagen being induced by treating chondrocytes with IL-1β, the decrease in inhibiting the expression of type II collagen and Sox-9 and the levels of the proteins, the decrease in the transcriptional activity of Sox-9, etc. (FIG. 2a), were recovered by LDR irradiation (FIG. 2b); and the phenomena of the increase in the level of COX-2 expression being induced by treating chondrocytes with IL-1β, the decrease in the level of I-κB protein, and the increase in the transcriptional activity of NF-κB (FIG. 2c) were also recovered by LDR irradiation (FIG. 2d).

Additionally, as a result of the analysis of the correlation of PI3K/Akt signaling regarding its inhibition against LDR-mediated chondrocyte destruction, it was confirmed that the levels of p38, which is activated by IL-1β treatment, and all the MAPK proteins such as c-Jun N-terminal kinase, did not change (FIG. 3a), but Akt activation (FIGS. 3b and 3c), which is closely associated with IL-1β-induced chondrocyte disorders, was shown to be inhibited by LDR irradiation (FIG. 3d).

Meanwhile, as a result of the analysis of the role of IL-1β-induced catenin proteins regarding the chondrocyte destruction, it was confirmed that, in the IL-1β-treated chondrocytes, the expressions of α-, β-, and γ-catenin proteins were induced in a time-dependent manner (FIG. 4a), the overexpression of catenin proteins in chondrocytes caused the inhibition of type II collagen and Sox-9 expression, induction of COX-2 expression, and decrease in I-κB protein level (FIG. 4b), decreased the Sox-9 activity while reducing the NF-κB activity (FIG. 4c), and the overexpression of catenin simultaneously with the IL-1β in the chondrocytes was shown to improve the effect compared to the IL-1β treatment alone (FIG. 4d).

Additionally, as a result of the analysis of an LDR effect with respect to the IL-1β-induced catenin expression and catenin-induced cartilage destruction, it was confirmed that LDR alone could not change the expression of catenin proteins (FIG. 5a), however, in the case of IL-1β treatment, LDR at doses of 0.5 cGy and 1 cGy reduced the IL-1β-induced expressions of all the catenin proteins (FIG. 5b) and reduced the levels of catenin proteins to the basal level before the IL-1β treatment (FIG. 5c), LDR recovered the expression of type II collagen and Sox-9 proteins in the catenin-overexpressing chondrocytes and inhibited the decrease of I-κB and COX-2 expression (FIG. 5d), LDR increased the Sox-9 activity in the catenin-overexpressing chondrocytes and reduced the transcriptional activity of NF-κB (FIG. 5e), and the BAY 11-7082, which is an NF-κB inhibitor, inhibited the decrease of I-κB in catenin-overexpressing chondrocytes in a dose-dependent manner, inhibited the expression of COX-2 compared to the IL-1β-treated chondrocytes (FIG. 5f), and reversed the decrease of I-κB and the induction of COX-2 expression (FIG. 5g).

Finally, as a result of the analysis of an LDR effect with respect to the soluble factor-induced chondrocyte destruction, it was confirmed that in the chondrocytes, where β- and γ-catenins were overexpressed, there occurred EGF-, PMA-, and RA-induced pathological changes, such as the inhibition of expression of type II collagen and Sox-9 proteins, and induction of COX-2 protein expression, but LDR irradiation was shown to recover the pathological changes (FIG. 6). From the foregoing results, it can be concluded that the method of the present invention, by utilization of LDR, can inhibit the damage, dedifferentiation, and inflammatory responses of chondrocytes.

In a specific aspect, the present invention provides a method for inhibiting inflammatory responses of chondrocytes including a step of irradiating the inflammation-induced chondrocytes of a subject with low-dose radiation (LDR).

Additionally, the present invention also provides a method for inhibiting dedifferentiation of chondrocytes including a step of irradiating the chondrocytes of a subject requiring the inhibition of the dedifferentiation of chondrocytes with low-dose radiation (LDR).

The chondrocytes, low-dose radiation, inflammatory response, and dedifferentiation are the same as described above.

More specifically, the range of the low-dose radiation used in the above method is not particularly limited as long as it is an amount of radiation that can inhibit the inflammatory responses, dedifferentiation, and/or destruction of chondrocytes when the chondrocytes are irradiated therewith, but it is preferably a minimum amount of radiation as long as it exhibits the above effect, and when applied to a subject, it may be in the range of greater than 0 Gy and 1 Gy or less, and specifically greater than 0 Gy and 0.5 Gy or less.

In the present invention, the term "subject" includes mammals such as cattle, pigs, sheep, chickens, dogs, and humans, and may include, without limitation, any subject where the inflammatory responses, dedifferentiation, or the destruction of chondrocytes can be inhibited according to the method of the present invention.

Additionally, the present invention provides a method for treating a disease of cartilage including a step of irradiating the damaged cartilage area of a subject having a disease of cartilage caused by the damage of chondrocytes with low-dose radiation (LDR).

The chondrocytes, low-dose radiation, and subject are the same as described above.

More specifically, the range of the low-dose radiation used in the above method is not particularly limited as long as it is an amount of radiation that can inhibit the inflammatory responses, dedifferentiation, and/or destruction of chondrocytes when the chondrocytes are irradiated therewith, but it is preferably a minimum amount of radiation as long as it exhibits the above effect, and when applied to a subject, it may be in the range of greater than 0 Gy and 1 Gy or less, and specifically greater than 0 Gy and 0.5 Gy or less.

As used herein, the term "a disease of cartilage" is also called a disease with cartilage damage, and refers to a disease that occurs as a result of damage in cartilage tissues and/or joint tissues (synovial membranes, articular capsules, subchondral bones, etc.) by a mechanical stimulus or inflammatory response. The disease of cartilage is not particularly limited as long as the disease can be treated by LDR irradiation of the present invention, but preferably, it may be degenerative arthritis, rheumatoid arthritis, fracture, damage to muscle tissues, plantar fasciitis, lateral epicondylitis, calcific tendinitis, nonunion of fracture, joint injuries due to trauma, etc.

Meanwhile, for the treatment of the disease of cartilage, in the present invention, on the damaged cartilage area may be irradiated with the provided LDR alone, or may be irradiated therewith along with an inhibitor of chondrocyte damage, such as other known arthritis agents, as a complex treatment. In particular, the arthritis agents, although not particularly limited, may preferably be analgesics, non-steroidal anti-inflammatory analgesics, steroids, COX-II inhibitors, cartilage regeneration-promoting agents, etc., and more preferably, nonsteroidal anti-inflammatory analgesics such as Indometacin®, Velden®, Surgam®, Naxen®, Voltaren®, Lodine®, Somalgen®, Airtal®, Brexin®, etc., or cartilage regeneration-promoting agents such as Udin®, Chondron®, Cartistem®, etc.

Additionally, when LDR irradiation is treated along with the inhibitor of chondrocyte damage, LDR irradiation may be performed after treatment with the inhibitor of chondrocyte damage or the treatment with the inhibitor of chondrocyte damage may be performed simultaneously while irradiating with LDR, but is not limited thereto.

[Mode for Invention]

Hereinafter, the present invention will be described in more detail with reference to the following Examples. However, these Examples are for illustrative purposes only, and the invention is not intended to be limited by these Examples.

Example 1: Effect of LDR on Chondrocytes

Since a high-dose radiation (HDR) in the range of 3 Gy to 10 Gy is known to induce pathological dysregulation of chondrocytes, the effect of low-dose radiation (LDR) of 2 cGy or less on the chondrocytes was examined.

First, the chondrocytes derived from joints were cultured in a DMEM medium according to a known method (E. H. Hong, et al., J. Biol. Chem. 285:1283-1295, 2010). Then, the cultured chondrocytes were inoculated into culture dishes at a density of $5 \times 10^4$ cells/cm$^2$, which were irradiated with 0 cGy, 0.5 cGy, 1.0 cGy, 1.5 cGy, and 2.0 cGy LDR using a $^{137}$Cs-ray source (KIRMS, Korea), and the levels of type II collagen or Sox-9 protein, which are cartilage-specific differentiation marker proteins, and I-κB or COX-2 protein, which are inflammation-related proteins, were determined via Western blot analysis, and the transcriptional activity of Sox-9 protein and NF-κB, which is affected by I-κB, were determined by reporter gene assay (FIGS. 1a and b).

First, as shown in FIG. 1a, LDR did not have any noticeable effect on the level of type II collagen or Sox-9 protein, which are cartilage-specific differentiation marker proteins (top), and also did not have any significant effect on the activity of Sox-9 protein (bottom). Additionally, as shown in FIG. 1b, LDR did not have any noticeable effect on the expression level of COX-2 protein, which is used as a primary mediator for cartilage inflammation, or the I-κB protein, which is an inhibitor of NF-κB transcription factor (top), and also did not induce or inhibit the transcriptional activity of NF-κB, which is involved in the control of the COX-2 protein (bottom).

Meanwhile, in order to confirm the morphological change in chondrocytes, the chondrocytes were treated with LDR or 6 Gy HDR, and observed under optical microscope (FIG. 1c, top), or the chondrocytes were stained with SA-β-gal (β-galactosidase) and observed under confocal fluorescence microscope (FIG. 1c, bottom). In particular, the SA-β-gal staining was performed as follows: the radiation-irradiated chondrocytes were fixed using a 3.7% formaldehyde solution for 10 minutes, and the fixative was removed using PBS. The cells were added with the SA-β-gal staining solution (1 mg/ML 5-bromo-4-chloro-3-indolyl β-D-galactoside, 40 mM citric acid/sodium phosphate buffer, pH 6.0, 5 mM potassium ferrocyanide, 5 mM potassium ferricyanide, 150 mM NaCl, and 2 mM MgCl$_2$) and allowed to react at an oven temperature in a CO$_2$-free atmosphere for 16 hours. As shown in FIG. 1c, when the chondrocytes were treated with LDR, the shape of chondrocytes did not change and did not show a positive reaction to SA-β-gal, and thus cell senescence was not induced, whereas when the chondrocytes were treated with HDR, the shape of chondrocytes changed into a flat shape and showed a positive reaction to SA-β-gal, thereby inducing cell senescence.

As such, in the chondrocytes irradiated with 2 cGy LDR or 6 Gy HDR for 3 hours, the levels of senescence-related proteins were evaluated according to time via Western blot analysis (FIG. 1d). As shown in FIG. 1d, when the chondrocytes were treated with 2 cGy LDR, the levels of p53 and p21 proteins, which are biochemical markers of senescence of chondrocytes, did not change even with the lapse of the irradiation time (top), whereas when the chondrocytes were treated with 6 Gy HDR, the levels of p53 and p21 proteins as the markers were shown to gradually increase with time (top). This confirms that LDR, unlike HDR, does not induce cell senescence.

Additionally, in order to examine the effect of LDR on the survival of chondrocytes, the number of chondrocytes was counted for a control group, wherein the chondrocytes were cultured for 48 hours without irradiation, and for sample groups, wherein the chondrocytes were irradiated with either 2 cGy LDR or 6 Gy HDR, according to the irradiation time, using a hemocytometer and a trypan blue solution (FIG. 1e, left). As shown in FIG. 1e (left), the number of chondrocytes in the control group and that in the sample group with LDR irradiation was increased according to culture time, but the number of chondrocytes in the sample group with HDR irradiation did not increase along with the culture time. In this regard, the apoptosis rate of chondrocytes in each group was calculated via analysis of the chondrocytes, after irradiation with 0 cGy, 0.5 cGy, 1.0 cGy. 1.5 cGy, and 2.0 cGy LDR for 48 hours followed by addition of propidium iodide (2.5 mg/mL) at room temperature for 5 minutes, using the FACScan flow cytometer (Becton Dickson, Franklin Lakes, N.J., USA) (FIG. 1e, right). As shown in FIG. 1e (right), the chondrocytes in the control group and the sample group with LDR irradiation showed the same level of apoptosis rate.

Finally, the effect of LDR irradiation on the possible DNA damage of chondrocytes was examined. In this regard, in order to confirm the presence of phosphorylation of γH2AX, which is a histone variant used as a DNA damage marker, for the chondrocytes in the control group, where the chondrocytes were not irradiated with radiation, and sample groups, where the chondrocytes were either irradiated with 2 cGy LDR for 30 minutes or 6 Gy HDR for 30 minutes, the antibodies to γH2AX were treated at a concentration of 10 μg/ml, and reacted for 1 hour for immunostaining, treated with rhodamine- or fluorescein isothiocyanate-conjugated secondary antibodies, and reacted for 1 hour. Additionally, the nuclei of the chondrocytes were stained with 4',6-diamidino-2-phenylindole to observe the presence of damage, and Merge staining was performed to confirm the presence of damage of the cytosol (FIG. 1f). As shown in FIG. 1f, the phosphorylation of γH2AX was not detected in both the control group and the sample group irradiated with 2 cGy LDR, and the damage of nuclei or cytosol was also not observed, regardless of the irradiation time, whereas, in the sample group irradiated with 6 Gy HDR, the phosphorylation of γH2AX was detected and the damage to nuclei or cytosol was also observed.

Summarizing these results, unlike HDR, which induces damage to chondrocytes, LDR in the range of 2 cGy or less was shown to be safe, not inducing any damage to the chondrocytes.

Example 2: Inhibitory Effect of LDR on IL-1β-Induced Chondrocyte Destruction

Chondrocytes were treated with either 10 ng/mL IL-1β alone, or in a combination of IL-1β treatment and 0.5 cGy or 1 cGy LDR, and the transcript levels of type I collagen, type II collagen, Sox-9, COX-2, and I-κB were measured via PCR using GAPDH as a control and a quantitative real-time PCR analysis, and the transcriptional activity of NF-κB was measured by reporter gene assay (FIGS. 2a, 2b, 2c, and 2d).

First, as shown in FIG. 2a, the treatment of chondrocytes with IL-1β alone induced the expression of fibrous type I collagen, inhibited the expressions of type II collagen and Sox-9, which is a major transcription regulator of type II collagen (top), and reduced the level of type II collagen and Sox-9 proteins (bottom), and the transcriptional activity of Sox-9 was reduced at 24 hours and 48 hours after IL-1β treatment, compared to control cells, by about 32% and 60%, respectively (middle). From the above, it was confirmed that IL-1β treatment promotes the dedifferentiation of chondrocytes.

Additionally, as shown in FIG. 2b, the irradiation of chondrocytes with 0.5 cGy or 1 cGy LDR after treatment enabled recovery of the expression level of type I collagen, whose expression was induced in the IL-1β-treated chondrocytes, and the expression levels of type II collagen and Sox-9 were recovered to their normal levels (top), the transcriptional activity of Sox-9, which was reduced in the IL-1β-treated chondrocytes, was increased by about 2.3- and 2.9-fold via 0.5 cGy and 1 cGy doses of LDR irradiation, respectively (middle), and also the levels of type II collagen and Sox-9, which were shown reduced in the IL-1β-treated chondrocytes, were completely recovered by LDR treatment (bottom). These results demonstrate that LDR provides a strong inhibitory effect against the IL-1β-treated dedifferentiation of chondrocytes.

Furthermore, as shown in FIG. 2c, as a result of the analysis of the effect of IL-1β treatment on the expression of COX-2, which is a target in the NF-κB pathway and primary mediator of cartilage inflammation, the level of COX-2 expression, at 24 hours and 48 hours after IL-1β treatment, increased by about 9.8- and 7.7-fold, compared to that of the control group (top); in the same condition, the level of I-κB protein, which is an inhibitor of NF-κB transcription factor, was rapidly decreased (middle); and the transcriptional activity of NF-κB, at 24 hours and 48 hours after IL-1β treatment, increased by about 8.6- and 6.7-fold, respectively (bottom).

Finally, as shown in FIG. 2d, the irradiation of chondrocytes with 0.5 cGy or 1 cGy LDR after IL-1β treatment recovered the level of COX-2 transcript, which was increased by IL-1β treatment, to its normal level, whereas the irradiation with 0.5 cGy or 1 cGy LDR decreased the level of COX-2 ml NA by about 70% and 80% compared to the IL-1β treatment alone (top); in the same condition, the level of I-κB protein, which was reduced in the IL-1β-treated chondrocytes, was recovered to its normal level (middle); and in the same condition, the level of transcriptional activity of NF-κB, which was increased in the IL-1β-treated chondrocytes, was also recovered to its normal level. However, the level of transcriptional activity of NT-κB in the chondrocytes treated by the irradiation with 0.5 cGy and 1 cGy LDR was decreased by about 76% and 83%, respectively, compared to that in the chondrocytes treated with IL-1β alone (bottom).

Summarizing these results, it was confirmed that LDR can inhibit the dedifferentiation and inflammation of chondrocytes induced by IL-1β treatment.

Example 3: Analysis of the Correlation of PI3K/Akt Signaling on the Inhibition of LDR-Mediated Chondrocyte Destruction In order to identify the mechanism by which LDR regulates chondrocyte phenotype, the levels of mitogen-activated protein kinase (MAPK) activation or Akt activation before and after LDR treatment were measured in the IL-1β-treated chondrocytes.

First, in a state where chondrocytes were either untreated (−) or treated with 10 ng/mL IL-1β (+), the chondrocytes were treated by the irradiation with 0.5 cGy or 1 cGy LDR, and the levels of expression and phosphorylation of ERK, p38, and INK were determined via Western blot analysis (FIG. 3a). As shown in FIG. 3a, p38, which is an extracellular signal-regulated kinase, all MAPK proteins such as c-Jun N-terminal kinase were activated by IL-1β treatment, this phenomenon was not changed by LDR treatment, and the results indicate that LDR-mediated regulation of the chondrocyte phenotype is achieved through a MAPK signaling-independent pathway.

Additionally, chondrocytes were treated or untreated with 40 μM triciribine, reacted for 1 hour, treated with 10 ng/mL IL-1β, and the levels of expression and phosphorylation of Akt and GSK3α/β were determined via Western blot analysis (FIG. 3b), As shown in FIG. 3b, it was confirmed that the IL-1β-treated chondrocytes induced the phosphorylation of Akt and then inactivated the glycogen synthase kinase 3β (GSK3β), which is a substrate for Akt (top), whereas triciribine, which is an Akt signaling pathway-specific inhibitor, markedly inhibited the phosphorylation of Akt increased by the IL-1β-treat treatment, and thereby reactivated GSK3β in the chondrocytes (bottom).

Meanwhile, chondrocytes were treated with LY294002, which is another chemical inhibitor of PI3K/Akt signaling, at a concentration of 10 μM or 20 μM, reacted for 1 hour, treated with 10 ng/mL, and reacted for 48 hours. Upon reaction, the levels of type II collagen, Sox-9, I-κB, and COX-2 proteins were determined via Western blot analysis, and the transcriptional activity of NF-κB was determined by reporter gene assay (FIG. 3c). As shown in FIG. 3c, in the IL-1β-treated chondrocytes. LY294002 led to the recovery of type II collagen and Sox-9 expression, reduction of COX-2 expression, and the inhibition of I-κB degradation (top), and 10 μM LY294002 and 20 μM LY294002 reduced the NF-κB activity by about 48% and 68% compared to the HAD-treated chondrocytes, respectively (bottom). These results demonstrate that Akt activation is closely associated with IL-1β-induced chondrocyte disorders.

Finally, in order to confirm whether LDR, is involved in the regulation of IL-1β-induced Akt activity, chondrocytes, which were in a state untreated (−) or treated with 10 ng/mL (+), were treated with 0.5 cGy or 1 cGy LDR for 12 hours, and upon completion of the reaction, the levels of expression of Akt and GSK3α/β and phosphorylation were determined via Western blot analysis (FIG. 3d). As shown in FIG. 3d, it was confirmed that 0.5 cGy and 1 cGy LDR irradiation could inhibit the Akt activation induced in the IL-1β-treated chondrocytes.

Summarizing these results, it was confirmed that LDR irradiation can block the IL-1β-induced PI3K/Akt signaling pathway instead of the MAPK pathway in articular cartilage, thereby inhibiting the destruction of IL-1β-treated chondrocytes.

Example 4: Role of IL-1β-Induced Catenin Proteins in Chondrocyte Destruction

The present inventors examined whether catenin proteins, which are involved in the downstream targets of Akt signaling of cell-cell adhesion and gene transcription, are also associated with chondrocyte destruction.

First, chondrocytes were treated with 10 ng/mL IL-1β for a predetermined period of time, and the levels of the catenin proteins were determined via Western blot analysis (FIG. 4a). As shown in FIG. 4a, in the IL-1β-treated chondrocytes, α-, β-, and γ-catenin proteins were expressed in a time-dependent manner.

Additionally, an ectopic overexpression was performed, in conditions where chondrocytes were untreated or treated with Sox-9, or untreated or treated with an NF-κB reporter gene, by introducing GFP-labeled S83A α-catenin, FLAG-labeled S33A β-catenin, or wild type γ-catenin. Then, the levels of differentiation- and inflammation-related proteins were determined via Western blot analysis (FIG. 4b), and the transcriptional activity of Sox-9 or NF-κB was determined by reporter gene assay (FIG. 4c). In particular, the ectopic overexpression of catenins was performed via transfection of chondrocytes with expression vectors using a GFP-labeled S83A point mutant of α-catenin generated by site-directed mutagenesis using wild type α-catenin as a template, a nonubiquitinatable FLAG-labeled S33A β-catenin purchased from Addgene, wild type γ-catenin, and Lipofectamine PLUS (Invitrogen). As shown in FIG. 4b, in chondrocytes, the ectopic overexpression of β-catenin binding-deficient mutant α-catenin, nonubiquitinatable mutant β-catenin, or wild type γ-catenin in chondrocytes caused the inhibition of type II collagen and Sox-9 expression, induction of COX-2 expression, and degradation of I-κB protein in all experiments. Additionally, as shown in FIG. 4c, the transfection of 3 ng of the α-, β-, and γ-catenin plasmids reduced Sox-9 activity by about 60%, 79%, and 63%, respectively, compared to the control group (FIG. 4c, top), and increased NE-κB activity by about 5.0-, 7.8-, and 6.0-fold, respectively (FIG. 4c, bottom).

Finally, chondrocytes were transfected with 3 μg of the respective catenin plasmid for 24 hours, and untreated (−) or treated with 10 ng/mL, IL-1β (+) for 48 hours. Then, the levels of differentiation- and inflammation-related proteins were determined via Western blot analysis, and the transcriptional activity of NF-κB at 24 hours after IL-1β treatment was determined by reporter gene assay (FIG. 4d). As shown in FIG. 4d, the simultaneous combined IL-1β treatment of chondrocytes and catenin overexpression therein inhibited the expression of type II collagen and Sox-9 proteins, induced the degradation of I-κB protein, and promoted the expression of COX-2 protein, exhibiting an even greater effect compared to IL-1β treatment alone (top), and the simultaneous combined IL-1β treatment of chondrocytes and overexpression of α-, β-, and γ-catenins increased NE-κB activity by about 12.4-, 15.5-, and 14.2-fold, respectively, whereas IL-1β treatment alone induced an about 8.5-fold increase (bottom).

Summarizing these results, it was confirmed that not only IL-1β but also catenin signaling plays a crucial role in the destruction of chondrocytes, and both mediate the IL-1β-induced dedifferentiation and inflammation.

Example 5: Effect of LDR on Expression of IL-1β-Induced Catenin and Catenin-Induced Cartilage Destruction First, it was examined whether LDR can directly regulate the expression of catenin proteins in chondrocytes. In this regard, chondrocytes, which were in a state untreated or treated with 10 ng/mL IL-1β, were irradiated at varied doses of LDR for 48 hours, and the levels of catenin proteins were determined via Western blot analysis (FIGS. 5a and 5h). As a result, as shown in FIG. 5a, the LDR treatment alone did not change the expression of catenin proteins, but as shown in FIG. 5b, in a condition where chondrocyte were pretreated with IL-1β, the LDR at doses of 0.5 cGy and 1 cGy was able to dramatically reduce the IL-1β-induced expression of all catenin proteins.

Additionally, chondrocytes, which were in a state untreated or treated with 10 ng/mL IL-1β, were unirradiated or irradiated with 1 cGy LDR for 48 hours, and subjected to immunostaining to detect the expression level of each catenin (scale: 50 μm) (FIG. 5c). In particular, for the immunostaining of each catenin, each chondrocyte was treated with antibodies to α-, β-, and γ-catenins at a concentration of 10 μg/mL and reacted for 1 hour. The resulting cells were treated with rhodamine- or fluorescein isothiocyanate-conjugated secondary antibodies, reacted for 1 hour, and the level of immunostaining was evaluated via confocal fluorescence microscope. As shown in FIG. 5c, the treatment of chondrocytes with IL-1β significantly increased the levels of all the tested catenin proteins in both the cytosol and nuclear regions compared to control cells. At a dose of 1 cGy LDR, the catenin expression in IL-1β-treated cells was inhibited to basal levels, suggesting that LDR can inhibit the IL-1β-dependent post-translational stabilization of catenin.

Finally, the possibility of reversing the dedifferentiation and inflammatory responses, which were induced by the overexpression of α-, β-, and γ-catenin proteins, in chondrocytes was examined.

First, chondrocytes were introduced with 3 μg of FLAG-labeled S33A β-catenin or wild type γ-catenin, irradiated with LDR at varied doses of radiation for 48 hours, and the levels of differentiation- and inflammation-related proteins were determined via Western blot analysis (FIG. 5d). As shown in FIG. 5d, LDR recovered the expression of type II collagen and Sox-9 proteins, and inhibited I-κB degradation and COX-2 expression, thus confirming that LDR has the effect of inhibiting the induction of potential dedifferentiation.

Additionally, the transcriptional activity of Sox-9 or NF-κB was determined by reporter gene assay, and the experimental results were indicated in terms of mean standard deviation (FIG. 5e). As a result, it was confirmed that LDR can increase the activity of Sox-9 in catenin-overexpressing chondrocytes while reducing the transcriptional activity of NF-κB. Specifically, as shown in FIG. 5e (left), 1 cGy LDR irradiation increased Sox-9 activity by about a 2.2-, 2.7-, and 2.4-fold compared to that in cells transfected with α, and γ-catenins, and, as shown in FIG. 5e (right), reduced NF-κB activity by about 74%, 78%, and 75%, respectively, thus confirming that LDR has the effect of inhibiting the induction of potential inflammation.

Moreover, in order to further confirm the role of NF-κB signaling in catenin-mediated induction of COX-2 expression, catenin-overexpressing chondrocytes were treated with the NT-κB inhibitor, BAY 11-7082. Specifically, chondrocytes were reacted for 1 hour with or without treatment with 5 μM or 10 μM BAY 11-7082 and treated with 10 ng/mL, IL-1β to react for 48 hours, and upon completion of the reaction, the levels of I-κB and COX-2 proteins were determined via Western blot analysis (FIG. 5f). As shown in FIG. 5f, it was confirmed that the pretreatment with BAY 11-7082 inhibited I-κB degradation in a dose-dependent manner and reduced COX-2 expression compared to IL-1β-treated chondrocytes.

Finally, chondrocytes were transfected with 3 μg of GFP-labeled S83A α-catenin, FLAG-labeled S33A β-catenin, or wild type γ-catenin, reacted with or without treatment with 5 μM or 10 μM BAY 11-7082 for 24 hours, and the levels of I-κB and COX-2 proteins were determined via Western blot analysis (FIG. 5g). As shown in FIG. 5g, the degradation of I-κB and induction of COX-2 in cells transfected with α-catenin (left), β-catenin (middle), and γ-catenin (right) were reversed by BAY 11-7082 treatment, suggesting that NF-κB signaling is downstream of the catenin pathway.

Summarizing these results, it was confirmed that LDR irradiation can inhibit catenin-induced dedifferentiation and inflammation in chondrocytes.

Example 6: Inhibitory Effect of LDR Against Soluble Factor-Induced Chondrocyte Destruction In order to examine whether the inhibitory effect of LDR on chondrocyte disorders is exclusively related to the responses to IL-1β, cells were treated with EGF, PMA, and RA, which are agents known to induce dedifferentiation of chondrocytes. Specifically, chondrocytes were treated or untreated with 10 ng/mL EGF(a), 10 nM PMA(b), and 1 μM RA(c) for 2 hours, treated or untreated with 0.5 cGy or 1 cGy LDR for 36 hours, and the levels of catenin proteins and differentiation/inflammation-related proteins were determined via Western blot analysis (FIGS. 6a, 6b, and 6c).

As shown in FIGS. 6a, 6b, and 6c (top), similarly as in dedifferentiation and inflammation of chondrocytes by IL-1β treatment, it was confirmed that the EGF-, PMA-, and RA-induced pathological changes, such as inhibition of expression of type II collagen and Sox-9 proteins and induction of COX-2 protein expression, were related to the increase in β- and γ-catenin expressions; as shown in FIGS. 6a, 6b, and 6c (bottom), both 0.5 cGy and 1 cGy LDR dramatically reduced the EGF-, PMA-, or RA-induced expressions of all catenin proteins, and the expression levels of type II collagen, Sox-9, and COX-2 proteins, which were changed by the treatment of the above materials, could be recovered. These results suggest that LDR plays an important role in inhibiting damage in chondrocyte phenotypes induced by different soluble factors.

From these results, it was confirmed that LDR irradiation can inhibit EGF-, PMA-, and RA-induced dedifferentiation and inflammation in chondrocytes.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

What is claimed is:

1. A method for inhibiting an inflammatory response in a chondrocyte comprising a step of irradiating the chondrocyte separated from a living organism with a low-dose radiation (LDR) in a range of between about 0 centigray (cGy) to about 2 cGy.

2. The method of claim 1, wherein the inflammatory response is induced by interleukin-1β (IL-1β), an epidermal growth factor (EGF), PMA (phorbol 12-myristate 13-acetate), retinoic acid (RA), or a combination thereof.

3. The method of claim 1, wherein the dedifferentiation is induced by interleukin-1β (IL-1β), an epidermal growth factor (EGF), phorbol 12-myristate 13-acetate (PMA), retinoic acid (RA), or a combination thereof.

4. The method of claim 1, wherein the method is conducted in vitro or ex vivo.

5. The method of claim 1, wherein irradiation of the low-dose radiation is performed for about 6 hours to about 90 hours.

6. A method for inhibiting dedifferentiation of a chondrocyte comprising a step of irradiating the chondrocyte separated from a living organism with a low-dose radiation (LDR) in a range of between about 0 cGy to about 2 cGy.

7. The method of claim 6, wherein the method is conducted in vitro or ex vivo.

8. The method of claim 6, wherein irradiation of the low-dose radiation is performed for about 6 hours to about 90 hours.

9. A method for inhibiting destruction of a chondrocyte comprising a step of irradiating the chondrocyte separated from a living organism with a low-dose radiation (LDR) in a range of between about 0 cGy to about 2 cGy.

10. The method of claim 9, wherein the method is conducted in vitro or ex vivo.

11. The method of claim 9, wherein irradiation of the low-dose radiation is performed for between about 6 hours to about 90 hours.

12. A method for treating a disease of cartilage which has a damaged cartilage area comprising a step of irradiating the damaged cartilage area of a subject having the disease of cartilage accompanied by damage to a chondrocyte with a low-dose radiation (LDR).

13. The method of claim 12, wherein the low-dose radiation is in a range of between about 0 Gy to about 1 Gy or less.

14. A method for inhibiting an inflammatory response in a chondrocyte comprising a step of irradiating the chondrocyte of a subject having inflammation of the chondrocyte with a low-dose radiation (LDR).

15. The method of claim 14, wherein the low-dose radiation is in a range of between about 0 Gy to about 1 Gy.

16. A method for inhibiting dedifferentiation of a chondrocyte comprising a step of irradiating the chondrocyte of a subject requiring the inhibition of dedifferentiation of the chondrocyte with a low-dose radiation (LDR).

17. A method of claim 16, wherein the low-dose radiation is in a range of between about 0 Gy to about 1 Gy.

* * * * *